US006763149B2

(12) United States Patent
Riley et al.

(10) Patent No.: US 6,763,149 B2
(45) Date of Patent: Jul. 13, 2004

(54) METHOD AND APPARATUS FOR CORRECTING CROSSTALK AND SPATIAL RESOLUTION FOR MULTICHANNEL IMAGING

(75) Inventors: James K. Riley, Redmond, WA (US); Keith L. Frost, Seattle, WA (US)

(73) Assignee: Amnis Corporation, Seattle, WA (US)

( * ) Notice: Subject to any disclaimer, the term of this patent is extended or adjusted under 35 U.S.C. 154(b) by 37 days.

(21) Appl. No.: 10/132,059

(22) Filed: Apr. 24, 2002

(65) Prior Publication Data

US 2003/0016882 A1 Jan. 23, 2003

Related U.S. Application Data

(60) Provisional application No. 60/286,713, filed on Apr. 25, 2001.

(51) Int. Cl.[7] .............................. G06K 9/32; G06K 9/68
(52) U.S. Cl. ........................ 382/294; 382/300; 382/218
(58) Field of Search .................................. 382/203, 218, 382/276, 277, 282, 287, 294, 300; 356/73, 317, 326; 345/58

(56) References Cited

U.S. PATENT DOCUMENTS

| 4,581,586 | A | * | 4/1986 | Rubin ........................ 329/308 |
| 4,770,992 | A | | 9/1988 | Van den Engh et al. ........ 435/6 |
| 5,096,807 | A | | 3/1992 | Leaback ........................ 435/6 |
| 5,365,525 | A | * | 11/1994 | Newberg et al. ............ 714/701 |
| 5,473,338 | A | * | 12/1995 | Prince et al. .................. 345/58 |
| 5,613,156 | A | | 3/1997 | Katayama .................... 395/827 |
| 5,848,123 | A | | 12/1998 | Strommer .................... 378/98.8 |
| 5,919,140 | A | | 7/1999 | Perelman et al. ............ 600/476 |
| 5,929,986 | A | | 7/1999 | Slater et al. ................. 356/326 |
| 5,988,862 | A | | 11/1999 | Kacyra et al. ............... 364/578 |
| 6,007,994 | A | | 12/1999 | Ward et al. .................... 435/6 |
| 6,014,468 | A | | 1/2000 | McCarthy et al. ........... 382/254 |
| 6,066,459 | A | | 5/2000 | Garini et al. .................... 435/6 |
| 6,072,765 | A | | 6/2000 | Rolland et al. .............. 369/128 |
| 6,134,283 | A | * | 10/2000 | Sands et al. ................. 375/354 |
| 6,210,973 | B1 | | 4/2001 | Pettit .......................... 436/172 |
| 6,211,955 | B1 | * | 4/2001 | Basiji et al. ................. 356/326 |
| 6,249,341 | B1 | * | 6/2001 | Basiji et al. ................... 356/73 |
| 6,381,363 | B1 | | 4/2002 | Murching et al. ........... 382/164 |
| 6,433,904 | B1 | * | 8/2002 | Swanson et al. .............. 398/91 |
| 6,452,707 | B1 | * | 9/2002 | Puc et al. .................... 398/158 |
| 6,522,781 | B1 | | 2/2003 | Norikane et al. ........... 382/203 |
| 6,553,044 | B1 | * | 4/2003 | Eden ........................ 372/38.02 |
| 6,662,332 | B1 | * | 12/2003 | Kimmitt ...................... 714/762 |
| 2001/0006416 | A1 | | 7/2001 | Johnson ........................ 356/73 |
| 2002/0126275 | A1 | | 9/2002 | Johnson ...................... 356/317 |

OTHER PUBLICATIONS

Kubota, Fumio et al. 1995. "Flow Cytometer and Imaging Device Used in Combination." *Cytometry*: 21:129–132.

(List continued on next page.)

*Primary Examiner*—Andrew W. Johns
*Assistant Examiner*—Amir Alavi
(74) *Attorney, Agent, or Firm*—Ronald M. Anderson

(57) ABSTRACT

A multichannel imaging system generates an ensemble of images for each field of view of an object. Each image in the ensemble is intended to contain information from only one source among a plurality of sources for the object. However, due to crosstalk, at least a portion of the signal from a first source appears in a channel intended for a second source. Because the accuracy of the correction will be degraded if the images in an ensemble are spatially misaligned with respect to one another, the spatial offset between images is determined and a correction is applied to substantially eliminate the offset. Then, a correction to the signals is determined to substantially reduce the contributions to the signal in a channel from the signals in other channels. The signal processing can be employed to process the output signals for each of a plurality of different disclosed imaging systems.

44 Claims, 27 Drawing Sheets

REALIGNMENT AND CROSSTALK CORRECTION
APPLIED TO MULTI-CHANNEL IMAGE

OTHER PUBLICATIONS

Kubota, F. 2003. "Analysis of red cell and platelet morphology using an imaging–combined flow cytometer." *Clin. Lab. Haem.*: 25:71–76.

Ong, S.H. and P.M. Nickolls. 1991. "Optical Design in a Flow System For Imagina Cells." *Sciences in Medicine*: 14:2:74–80.

Ong, S.H. and P.M. Nickolls. 1994. "Analysis of MTF Degradation in the Imaging of Cells in a Flow System." *International Journal of Imaging Systems & Technology*: 5:243–250.

Satoh, Kaneo et al. 2002. "Small Aggregates of Platelets Can Be Detected Sensitively by a Flow Cytometer Equipped With an Imaging Device: Mechanisms of Epinephrine–Induced Aggregation and Antiplatelet Effects of Beraprost." *Cytometry*: 48:194–201.

Wang, Fu–sheng and Fumio Kubota. 2002. "A Novel Apoptosis Research Method With Imaging–Combined Flow Cytometer and HITC OR IR–125 Staining." *Cytometry*:50:267–274.

Wietzorrek, Joachim et al. 1999. "A New Multiparameter Flow Cytometer: Optical and Electrical Cell Analysis in Combination With Video Microscopy in Flow." *Cytometry*: 35:291–301.

* cited by examiner

ILLUSTRATION OF CROSSTALK IN
MULTICHANNEL IMAGING SYSTEM

*OVERALL ALGORITHM STRUCTURE*

*APPLYING SPATIAL AND SPECTRAL CORRECTIONS*

*COMPUTE SPATIAL OFFSETS BETWEEN CHANNELS*

*BUILDING THE AVERAGE CORRELOGRAM*

*2-DIMENSIONAL GRADIENT OPERATOR*

*EFFECT OF THE GRADIENT OPERATION*

CONVOLUTION AS MULTIPLICATION IN THE
FREQENCY DOMAIN

IMAGES TO BE REALIGNED

CORRELOGRAM OF THE
MISALIGNED IMAGES

PIXEL DESIGNATIONS FOR
CORRELOGRAM SURFACE
DERIVATIVES

*COEFFICIENT MATRIX FOR 3X3 INTERPOLATION*

3X3 IMAGE ALIGNMENT COEFFICIENT MATRIX FOR TWO CASES

REALIGNMENT AND CROSSTALK CORRECTION
APPLIED TO MULTI-CHANNEL IMAGE

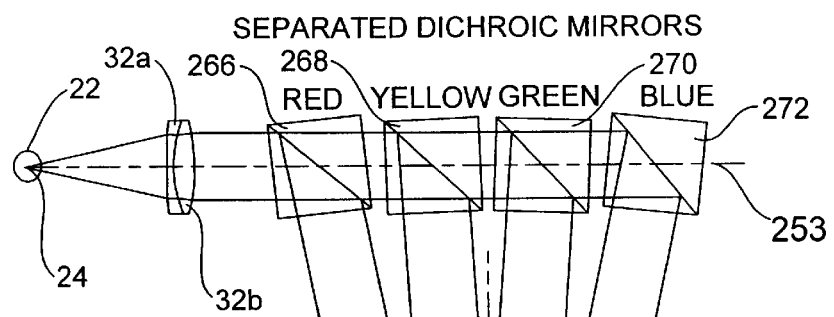
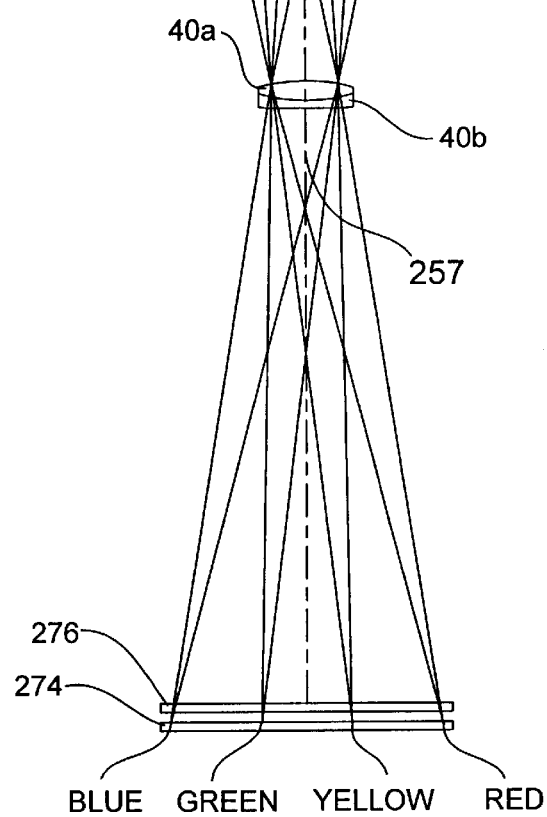
*FIG. 29*

METHOD AND APPARATUS FOR CORRECTING CROSSTALK AND SPATIAL RESOLUTION FOR MULTICHANNEL IMAGING

RELATED APPLICATION

This application is based on a prior copending provisional application Serial No. 60/286,713, filed on Apr. 25, 2001, the benefit of the filing date of which is hereby claimed under 35 U.S.C. §119(e).

FIELD OF THE INVENTION

The present invention generally relates to a method and apparatus for improving the accuracy of quantitative images generated by multichannel imaging instruments, and more specifically, to correcting errors introduced by crosstalk between channels, with application to a broad range of imaging instruments and particularly, to flow imaging instruments using time-delay-integration image detectors.

BACKGROUND OF THE INVENTION

The parallel advancement of the technology of video microscopy and techniques for preparing and staining biological samples has enabled those working in areas such as fundamental biological science, diagnostic medicine, and drug discovery to gather an ever-increasing amount of information from a single biological specimen. In the fields of cell biology and clinical cytology, for example, specimens may be stained with absorption dyes to define cell morphology, and with fluorescent dyes that attach to molecules bound to specific proteins or nucleic acid chains. Microscopes equipped for exciting and imaging the fluorescent dyes and concurrently imaging cell structures are routinely used for studying complex processes that modify cells on the gross structural level and also at the molecular level. In recent years, computational analysis of images captured from multiparameter microscopes has shown promise for automating large investigative studies such as those conducted by drug discovery and development companies and for automating complex cellular diagnostic tests for clinical medicine. Optimal use of such technology can be attained only if the signals used for image generation are accurately scaled to information about the cells being studied. However, such information can be degraded during the capture process. Specifically, interference can be introduced into a channel dedicated to a first signal due to leakage of a signal intended for a second channel. This type of signal degradation is generally referred to as channel-to-channel crosstalk.

An advancement to computer-based multiparametric imaging is disclosed in commonly assigned U.S. Patents, both entitled IMAGING AND ANALYZING PARAMETERS OF SMALL MOVING OBJECTS SUCH AS CELLS, U.S. Pat. No. 6,249,341, issued Jun. 19, 2001 (filed Jan. 24, 2000), and U.S. Pat. No. 6,211,955, issued Apr. 3, 2001 (filed Mar. 29, 2000), the complete disclosure, specification, and drawings of both of which are hereby specifically incorporated herein by reference. The technology disclosed in these applications extends the methods of computer vision to the analysis of objects either flowing in a fluid stream or moving relative to the imaging instrument on a rigid substrate, such as a glass slide. Instruments based on the inventions of the patent applications cited above deliver improved sensitivity at high spatial resolution through the use of time-delay-integration (TDI) electronic image acquisition, a method wherein signal integration is accomplished by shifting charge packets through an imaging array in synchrony with the motion of the target object being imaged.

The TDI-based flow imaging technology, with its ability to substantially improve signal-to-noise ratio, is of exceptional utility for multiparametric imaging. Each of the channels of a TDI flow imaging instrument can be dedicated to a single light source in the target objects. One such light source, for example, is the fluorescent dye attached to a molecule selected for its specificity for binding to a target protein. Each of a plurality of channels can be dedicated to a particular different dye, and all of the dyes addressed by the instrument may be present in close proximity on a single target cell. Because the dyes may have emission spectra broader than the passbands of the channels that collect their signals, channel-to-channel crosstalk can prevent the accurate estimation of the intensity of the signal from each dye.

Accordingly, it would clearly be desirable to develop a method and apparatus that simultaneously offers speed and accuracy in eliminating such channel-to-channel crosstalk. Preferably such crosstalk reduction can be achieved in conjunction with the TDI-based flow imaging method and apparatus noted above, which are intended for real time collection and processing of images from objects moving in high concentration, at high speed, through the instrument. Accordingly, the crosstalk reduction of the present invention is preferably applicable in real time and in synchrony with the collection of images of the moving targets that include indicators attached to the targets.

SUMMARY OF THE INVENTION

The present invention is directed to enabling an accurate reconstruction of information about objects imaged by an instrument using multiple channels, each channel being generally optimized to receive signals of a type differentiated from other signal types by predefined characteristics. These predefined characteristics may include, but are not limited to wavelength, a modulation of a signal received from a source, a scatter angle, a Doppler shift, and a phase shift (e.g., with respect to a reference phase). The present invention applies to, but is not limited to, instruments for collecting information from electromagnetic waves in all portions of the spectrum, by acoustic waves, by particle flux, and by measurement of object characteristics such as conductivity, chemical reactivity, size, shape, and mass.

One example of an application of the present invention is its use in a multiple-wavelength optical imaging instrument. In such an instrument, each channel is made sensitive to electromagnetic radiation of wavelengths bounded by an upper and lower limit, defining different wavebands for each channel. Typically these limits are determined by the characteristics of one or more filters disposed in a path between a light source and a photodetector servicing a channel. The images in each channel are detected, producing signals that are processed by the present invention to correct errors in alignment between the channels and a reference and then, to correct for crosstalk between the channels.

Thus, the present invention is directed to a method and apparatus that not only corrects for crosstalk between channels, but also ensures that signal data in each channel is properly aligned with signal data in other channels, so that the benefit from the crosstalk correction is not degraded by signal misalignment.

In one preferred embodiment, a method is provided for correcting signal misalignment between individual channels in a multichannel imaging system, such that data in a first channel is substantially aligned with data in other channels. The method also includes the step of reducing erroneous contributions to signal data from a source intended to provide signal data for other channels.

Preferably, the signal data are used to produce an image for display. Accordingly, a preferred embodiment is directed to a method that includes the step of spatially aligning images input in an image ensemble from a plurality of channels, such that each image in the image ensemble is substantially aligned with other images in the image ensemble, and the step of applying spectral crosstalk corrections, to remove the channel-to-channel crosstalk from the image ensemble output.

In one embodiment, the step of spatially aligning images includes the step of utilizing two classes of information, including a first and second class of constants. The first class of constants includes horizontal and vertical spatial offsets, which are derived from an on-line calibration image. The second class of constants is accessed during the step of spatially aligning images, but is not modified. Preferably the second class of constants includes at least one of channel start columns for each image, and inverted source coefficients.

The horizontal and vertical spatial offsets are preferably generated based upon a comparison of each image in an image ensemble with a calibration image. The comparison with a calibration image can be performed when a system for generating the multichannel signal is initialized, and/or periodically during the use of a system for generating the multichannel signal.

The step of generating the horizontal and vertical spatial offsets can include the steps of detecting a boundary of an image, preparing a correlogram based on the boundary and a reference image, determining a peak of the correlogram, and repositioning the image to correspond to a pixel closest to the peak of the correlogram.

Preferably the horizontal and vertical spatial offsets are determined for each pixel of the image, and the detection of the boundary of an image involves the use of a two-dimensional gradient operator to suppress flat surfaces and to enhance object boundaries. In one embodiment, preparing the correlogram based on the boundary and the reference image involves preparing a correlogram in the spatial domain, while in other embodiments the correlogram is prepared in the frequency domain.

In an embodiment in which the correlogram is prepared in the spatial domain, a Fourier Transform is performed on boundary data for the image and the reference image. Those results are multiplied to generate a product, and an inverse Fourier Transform is performed on that product.

To prepare the correlogram based on the boundary and the reference image in the frequency domain, first a Fourier Transform is performed on the boundary data for the image and the reference image. Then a conjugation operation is applied to one of the results of the Fourier Transforms. Next, the result of the conjugation operation is multiplied with the boundary data for the image to generate a product, and an inverse Fourier Transform is performed on the product.

To minimize errors, groups of images in each data channel are preferably processed together, such that a cumulative correlogram is generated for each data channel.

Once the correlogram is complete, the peak of the correlogram defines the aligned position of the image, relative to the reference image employed. The peak of the correlogram is determined by employing a Taylor series expansion, eigenvalues and eigenvectors. The image is then manipulated to align, to the nearest pixel, with that peak. Then, the image is reconstructed by interpolating to a fraction of a pixel, to align within a fraction of a pixel, with the true peak of the correlogram. Preferably, the interpolation involves the step of applying a two-dimensional interpolation.

In one embodiment, the step of applying a two-dimensional interpolation includes the step of computing a new amplitude value for each pixel based on a weighted sum of a group of surrounding pixels. Preferably, the weighted sum is determined by a Taylor series expansion based on a group of nine pixels, eight pixels of which surround a common origin pixel. Coefficients are applied to each pixel value, and the sum of a matrix of the coefficients is equal to 1.0.

The step of reducing erroneous contributions to that channel's measurement by sources intended for other channels preferably involves solving a set of linear equations relating source values to measurement values, wherein each channel is represented by a linear equation. It is also preferred that the set of linear equations are solved for each pixel in each image in each channel. The set of linear equations relating source values to measurement values can be solved by applying singular value decomposition to a matrix form of the set of linear equations.

The signal data, and/or corresponding images, can be spatially aligned in real-time. After the spatial alignment is completed, spectral crosstalk corrections can also be applied in real-time, or after the signal data/images have been stored for a period of time. The signal data/images can also be spatially aligned after having been stored for a period of time.

Another aspect of the present invention relates to a method for correcting errors in a multichannel imaging system, wherein each channel is intended to contain signal information relating to an image of an object that has been produced by only one type of source. The method involves focusing light from the object along a collection path, and dispersing the light that is traveling along the collection path into a plurality of light beams, such that each light beam corresponds to a single source. Each of the light beams is then focused to produce a respective image corresponding to that light beam. A detector is provided, disposed to receive the respective images. The detector generates an output signal corresponding to each image. For each output signal, a signal alignment correction and a crosstalk correction are applied.

In addition to the aforementioned embodiments relating to the method, the present invention also relates to a system having elements that carry out functions generally consistent with the steps of the method described above. One such system relates to a multichannel imaging system for generating an ensemble of images from an object for each field of view, wherein each image in the ensemble contains information from substantially only one type of source. The system includes a collection lens disposed so that light traveling from the object passes through the collection lens and travels along a collection path, and a dispersing component disposed in the collection path so as to receive the light that has passed through the collection lens, dispersing the light into a plurality of separate light beams, each light beam being directed away from the dispersing component in a different predetermined direction. The system also includes an imaging lens disposed to receive the light beams from the dispersing component, thereby producing the ensemble of images. The ensemble comprises a plurality of images corresponding to each of the light beams, each image being projected by the imaging lens toward a different predetermined location. A multichannel detector is disposed to receive the plurality of images produced by the imaging lens, and produces a plurality of output signals, such that a separate output signal is produced for each of the separate light beams. Finally, the system includes means for processing each output signal, wherein the means performs the functions of correcting output signal misalignment between individual channels, such that an image generated by an output signal in each channel is substantially aligned with a corresponding image in each other channel, reducing erroneous contributions to that channel's measurement by sources intended for other channels.

The system also preferably includes a display electrically coupled to the means, the display generating an image for each output signal as modified by the means. The means for processing preferably includes a memory in which a plurality of machine instructions defining a signal conditioning application are stored, and a processor that is coupled to the memory to access the machine instructions, and to the display. Execution of the machine instructions by the processor cause it to spatially align images that are displayed, based on the output signals from the multichannel detector, such that each image is substantially aligned with other images. The processor also applies the spectral crosstalk corrections, to remove the channel-to-channel crosstalk from the displayed images.

It is further contemplated that the means for processing the signal alternatively comprise a programmed computer, an application specific integrated circuit, or an oscilloscope.

Yet another embodiment of the system includes a plurality of different detectors, such that an image corresponding to a different source is directed to each detector, and the plurality of different detectors collectively comprise the multiple channels. The detectors employed in this embodiment of the system are preferably pixilated. For example, a TDI detector can beneficially be employed to produce output signals by integrating light from at least a portion of an object over time, while relative movement between the object and the imaging system occurs.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 27:
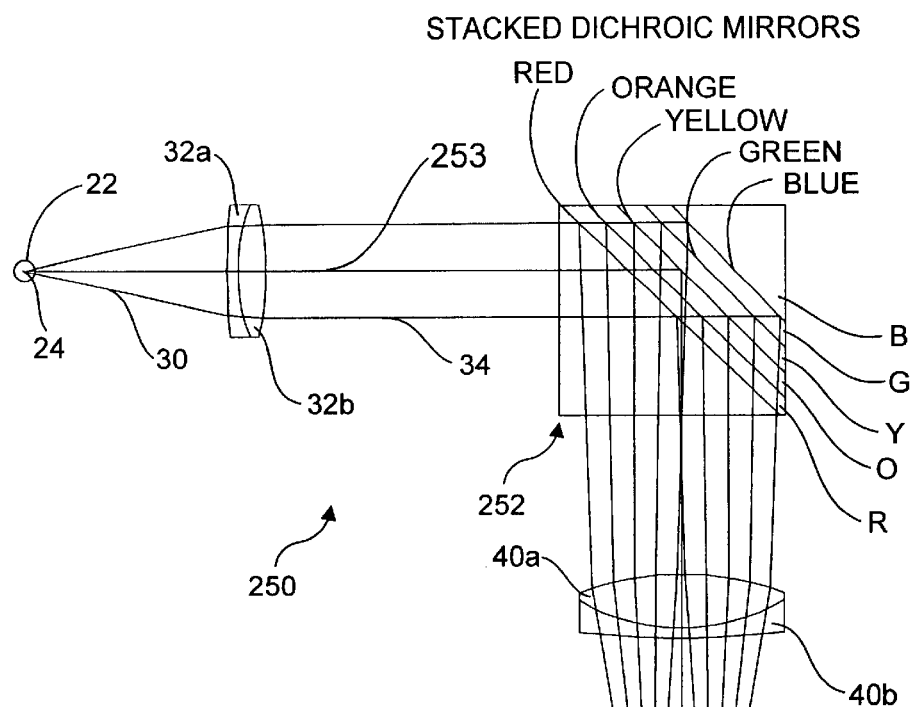
FIG. 27 is a plan view of an alternate embodiment that employs a spectral dispersion component comprising a plurality of stacked dichroic filters employed to spectrally separate the light from an object.
Figure 28:
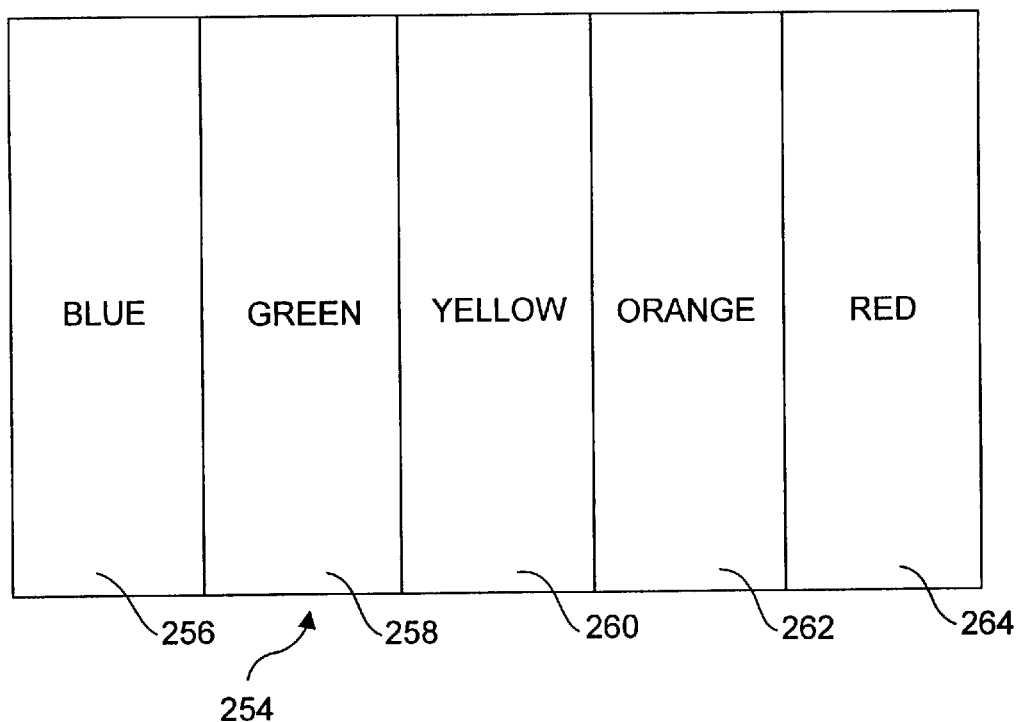

FIG. 28 is a schematic illustration of a detection filter assembly that may optionally be disposed in front of the TDI detector in the embodiment of FIG. 27 to further suppress out-of-band light; and FIG. 29 is a plan view of another embodiment of the configuration of FIG. 27, wherein the spectral dispersion filter system comprises a plurality of dichroic cube filters orientated at various different angles to create the spectral dispersing effect.

DESCRIPTION OF THE PREFERRED EMBODIMENT

Figure 1:
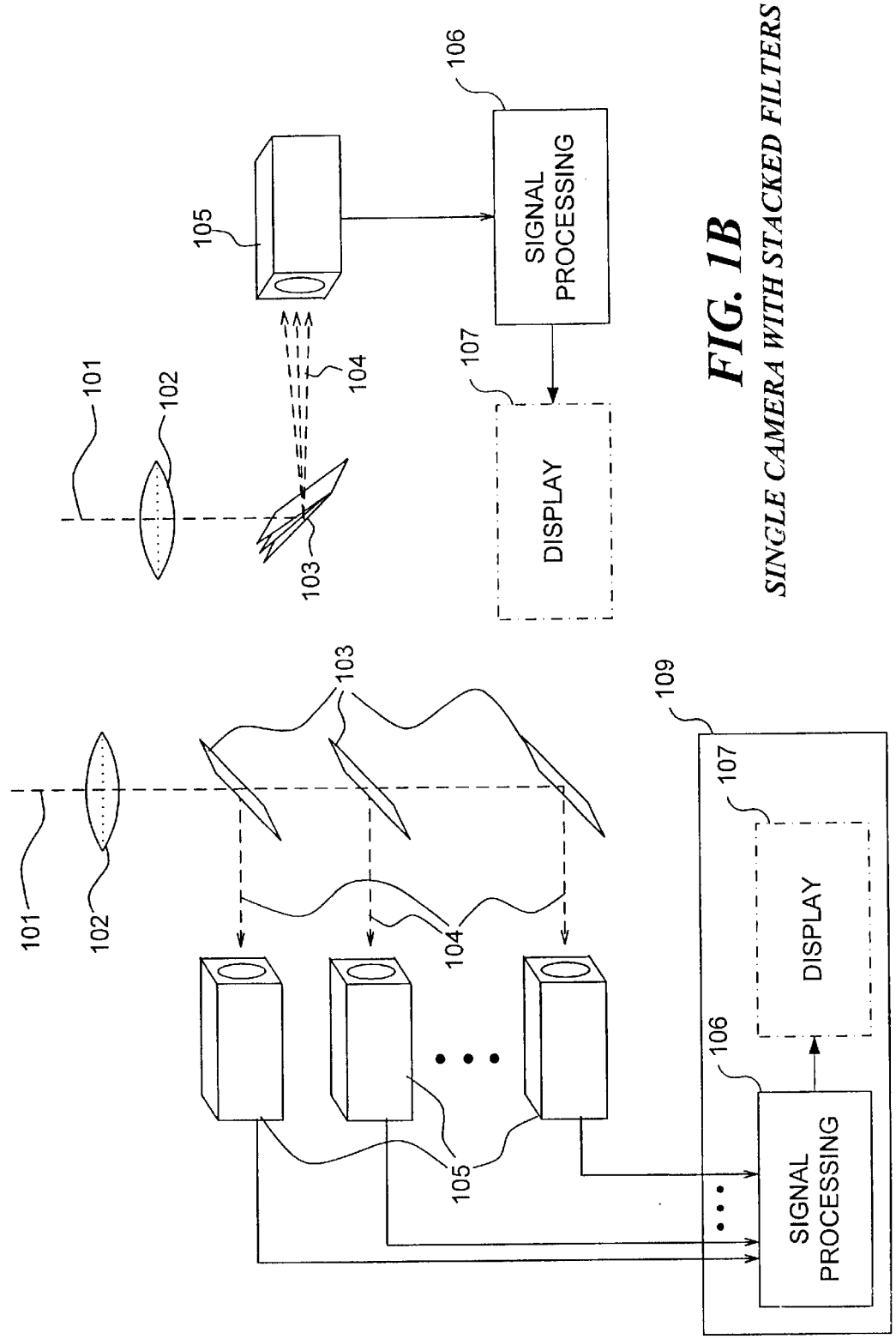
FIG. 1A is a schematic diagram of an image collection and capture system of a multichannel optical imaging instrument that includes a plurality of cameras, with one camera and one filter per channel.
FIG. 1B is a schematic diagram of an image collection and capture system for an optical imaging system accomplishing multiparametric imaging with a single camera and a plurality of filters.

FIGS. 1A and 1B illustrate two configurations of an instrument for implementing the present invention. FIG. 1A shows an embodiment that utilizes a plurality of photosensitive cameras 105. Lens 102 is used to form images on the photosensitive detector arrays of cameras 105. The light along each image formation path 101 is filtered by specially designed mirrors 103 that transmit light in a first range of wavelengths and reflect light in a second range of wavelengths, defining a plurality of different wavebands that are received by individual cameras 105. The signals from cameras 105 are processed by signal processing means 106, which aligns the signals relative to each other, and reduces crosstalk between signals. An optional element is a display 107, on which the plurality of images corresponding to the processed signals can be displayed to a user.

While display 107 will often be beneficially incorporated in such a system, such a display is not required. For example, a user may desire to collect data, process that data with signal processing means 106, and then store the processed data for display at a later time. It is further contemplated that signal processing means 106 and display 107, which are enclosed in a block 109, can be employed to process data (i.e., a multichannel signal) that was previously generated and stored for a period of time. Of course, signal processing means 106 can be employed to process the multichannel signal at any time after the signal has been generated, and the processed signals (aligned and corrected for crosstalk) can then be stored for a period of time before being displayed on display 107 (or further processed). Thus, while the imaging systems shown in FIGS. 1A and 1B represent exemplary preferred embodiments in which the present invention is applied, it should be understood that signal processing means 106 can be incorporated into many other different types of systems that generate a multichannel signal, or even used alone to process previously generated multichannel signals.

Signal processing means 106 ensures that the signals from a multichannel source are aligned relative to each other and reduces crosstalk among the signals from the multichannel source. The manner in which each of these functions is implemented is described in more detail below. Signal processing means 106 preferably comprises a programmed computing device, that includes a microprocessor and a memory in which machine instructions are stored that cause the microprocessor to appropriately process the signals. Alternatively, the signal processing means can comprise an application specific integrated circuit (ASIC) chip that employs hardwired logic for carrying out the processing functions, or a digital oscilloscope that can be configured to provide the required signal processing capability.

An alternative configuration for an imaging system usable with the present invention is shown in FIG. 1B. In this configuration, a single camera 105 is used to form an image in which light from a plurality of sources is filtered and reflected by a set of mirrors 103. Each mirror reflects light in a different waveband, forming a plurality of images in corresponding different regions of the camera's photosensitive array. The light reflected by the first mirror in incident on a first region, while the light transmitted by the first mirror in the stack falls on the face of the second mirror, which reflects light onto a second region of the camera's photosensitive detector. The successive reflection and transmission by the mirror stack produces a plurality of spectrally separated images, and single camera 105 produces a multichannel signal corresponding to those images formed on each region of the camera's photosensitive detector. These different signals are processed by signal processing means 106 and optionally displayed on display 107.

Figure 2:
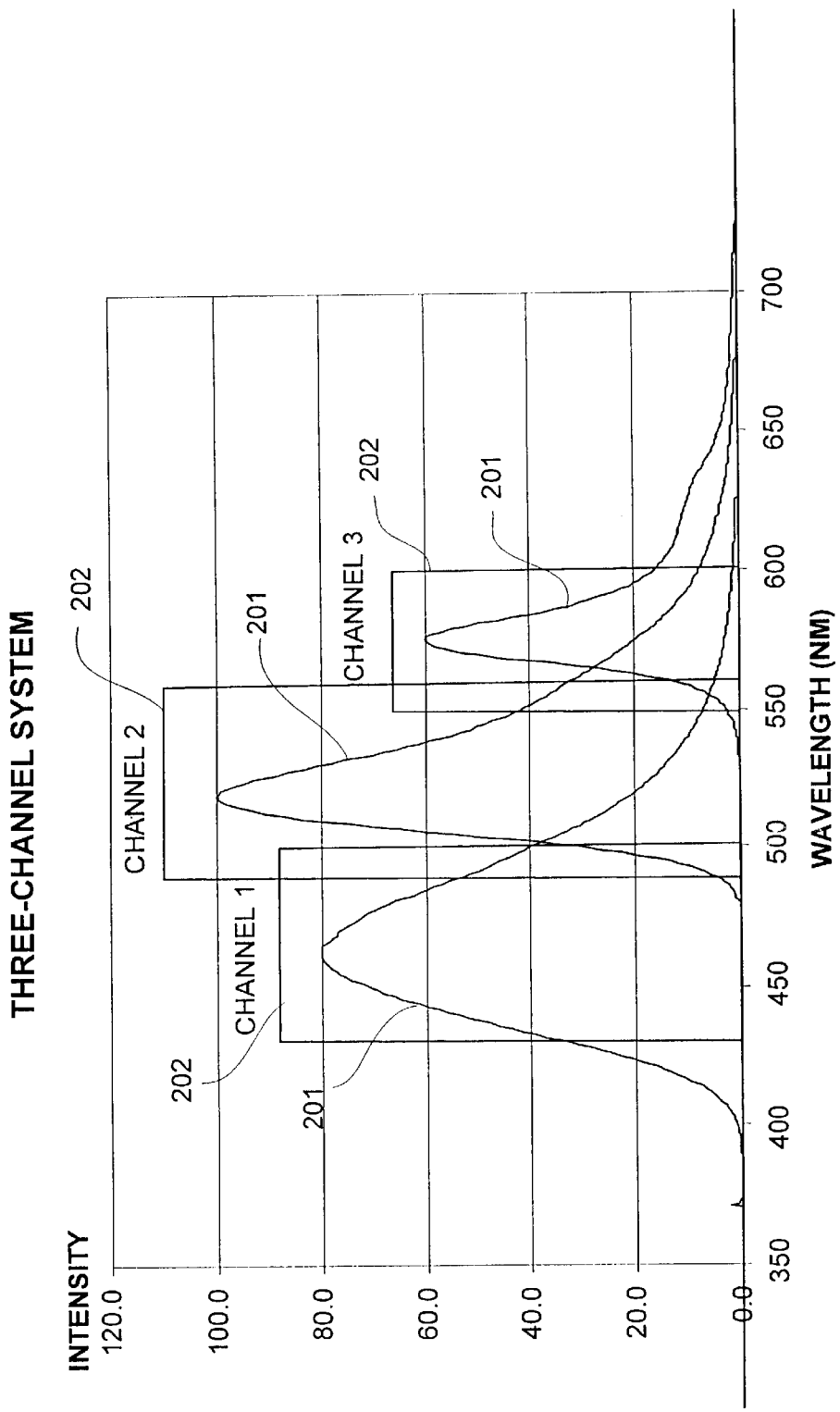
FIG. 2 is a graph of wavelength vs. intensity for three optical signal spectra and idealized passbands of corresponding bandpass filters.

Preferably, the light being imaged by the imaging systems of FIGS. 1A and 1B comprises wavelengths entirely encompassed within the passbands of the various channels. In that case, each color of light, such as red, contributes to only one image (e.g., an image of an object that is the source of the color of light in that channel). In many practical applications of the present invention, however, the light that forms images in each channel spans a range of wavelengths broader than the passband of an associated filter for the channel, as shown in FIG. 2. In this example, light 201 from each source is received in three channels 202. The signal conveyed in each channel is then a composite of information for the multiple sources. The object of the present invention is to process the signals from the plurality of channels to deliver the information for each source when displaying the image for that source.

It will be understood that many other multichannel imaging systems can benefit from the reduction in crosstalk provided by the present invention. FIGS. 17–29, which are described in detail below, illustrate examples of additional embodiments of multichannel imaging systems with which signal processing means 106 can be employed, to reduce crosstalk between channels.

In optical imaging systems that produce images of an object, the object may modify incident light by absorption of specific wavelengths, by absorption of the incident light followed by emission of light at a different wavelength, by diffraction of the incident light, or by refraction of the incident light. An object can also emit light without being excited using incident light. Each channel of a multichannel imaging instrument is designed to produce images formed in response to the light from an object produced in one of these ways. The present invention can be employed to enhance the contrast of such images.

In the present invention, the separation of signals from a detector into their proper channels is accomplished by solving a set of linear equations.

$$s_1 = \alpha_{11} m_1 + \alpha_{12} m_2 + \alpha_{13} m_3$$

$$s_2 = \alpha_{21} m_1 + \alpha_{22} m_2 + \alpha_{23} m_3,$$

and $$s_3 = \alpha_{31}m_1 + \alpha_{32}m_2 + \alpha_{33}m_3 \quad (1)$$

where $m_j$ is a measurement from channel j, $s_i$ is a characteristic parameter of source i, and $\alpha_{ij}$ is a weighting coefficient for source i into channel j.

These equations are solved using conventional methods of linear algebra, wherein the variables $s_i$, and $m_j$ are vectors and the variables $\alpha_{ij}$ comprise a matrix. The general term for this process is "crosstalk correction," since it removes the information from a source that has spilled over into a channel adjacent to the correct channel. This information spillover is analogous to crosstalk in bundled telephone lines, which results in a listener hearing a conversation from another line.

This set of equations must be solved for each pixel location in an image. It is essential that the images from all of the channels be precisely aligned with one another so that the correct values are entered into the equations for each pixel location. Therefore, a computational process is applied to the images corresponding to the field of view before the crosstalk correction is applied. The "field of view" is the scene captured in an image. The images belonging to a field of view are referred to herein as the "image ensemble" for that field of view.

Figure 3:
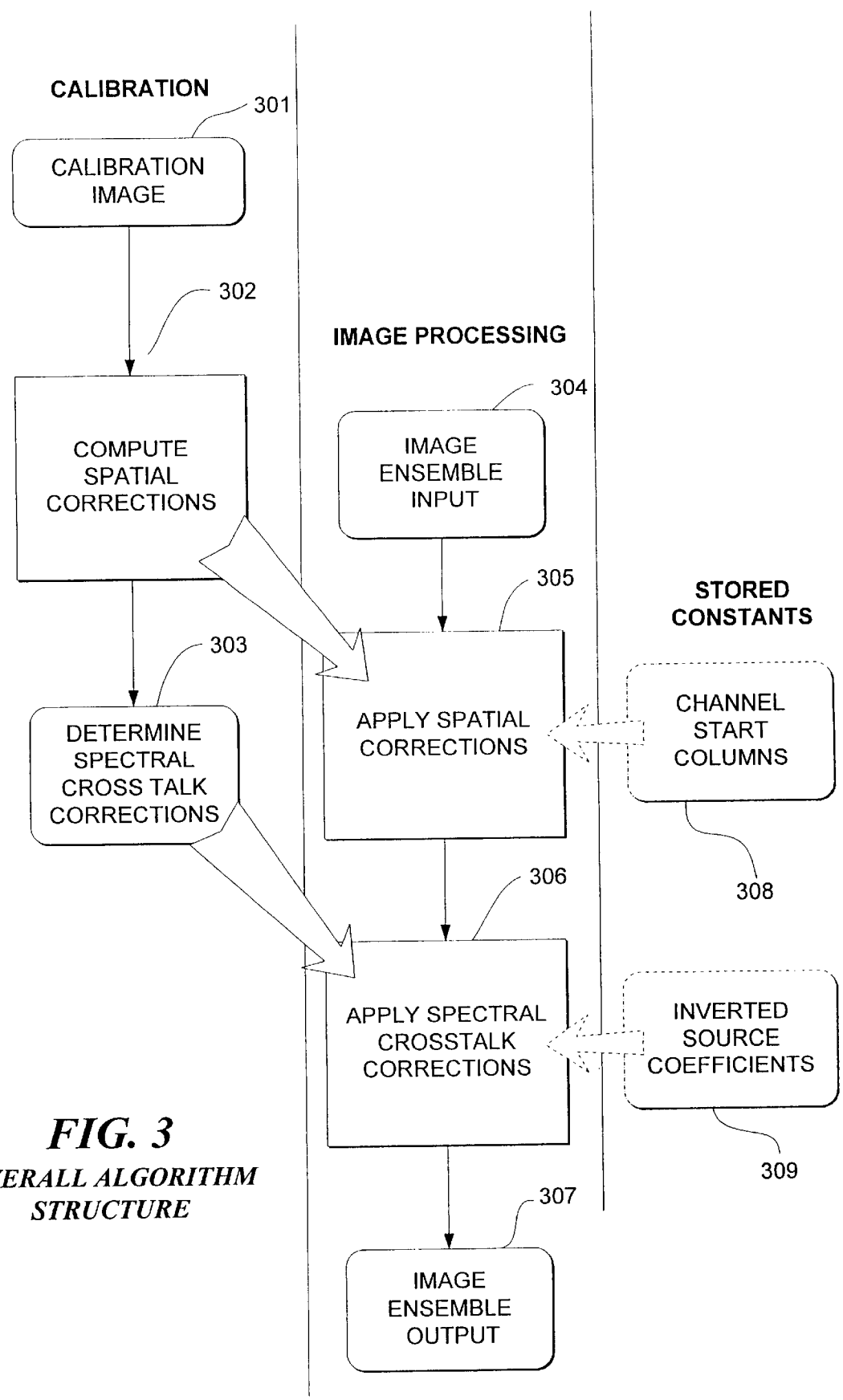
FIG. 3 is a flow chart showing the logical steps generally implemented in the crosstalk correction method of the present invention.

FIG. 3 illustrates the core processes carried out in the present invention and encompasses various signal processing stages, including calibrating for spatial correction parameters calibrating for spectral correction parameters and producing image ensemble outputs. The image ensemble outputs incorporate both a first spatial correction and a second spectral correction. First, the spatial correction parameters are determined, then the spectral correction parameters are determined, and finally image ensemble outputs are generated that incorporate both the spatial and spectral corrections. It should be noted that FIG. 3 illustrates the data flow used in the present invention, as opposed to a graphical depiction of a sequence of logical steps.

The stage of calibrating for spatial correction parameters is represented by a block 301. In block 301, a calibration image is obtained from actual biological specimens, or artificial specimens (e.g. flow beads). In a preferred embodiment, the calibration image corresponds to a reference channel selected from among a plurality of parallel channels. Most preferably, the reference channel is a bright field channel, with the balance of the channels representing fluorescence channels. In such an embodiment, the calibration image from the reference channel is actually part of the ensemble of images. Thus, the spatial offsets are generated in real time. It is contemplated that a calibration image could be utilized before image ensemble data correlating to actual samples are generated. In such a case, the spatial offset is not "live," but instead is based on the offsets determined with respect to the different channels corresponding to a calibration image that is not part of the image ensemble in regard to sample data. Because such offsets are not determined "live," it is anticipated that offsets determined in such an embodiment will not be as precise as those determined when the calibration image is actually part of the image ensemble corresponding to a particular sample. This approach should be less computationally expensive, and can be beneficially employed when previous data corresponding to similar indicate that little error would be introduced by using stored rather than live offset data.

Referring once again to FIG. 3, the algorithm computes the spatial correction parameters in a block 302. Once the spatial correction parameters are computed, the spectral correction parameters are generated in a block 303. Note that the spectral calibration process requires the use of a control, whereas any sample can be used to provide spatial correction data. The control is preferably a biological specimen or an artificial specimen to which a single known fluorophore has been attached. The fluorophore selected preferably has the characteristic of having a fluorescent signature primarily limited to a single one of the multi-channels. Some small amount of "spill over" from the single fluorophore will likely exist in the other channels. Based on the known spectral signature of the control, and the multi-channel data corresponding to that control, spectral corrections can be determined to eliminate such spill over, or crosstalk. Such a control is also referred to as a single source, because its spectral signature is substantially confined to a single channel. A control can be imaged alone, as part of a calibration phase that occurs before acquiring data from samples. In at least one embodiment, a control is introduced into a batch of samples, so that the calibration can occur during the processing of a batch on samples.

Once the spatial and spectral correction factors have been determined, the signal processing can be performed on the ensemble of images. In a block 304 the ensemble of images are input. The spatial corrections (determined in block 302) are applied to the ensemble of images in a block 305. Next, the spectral crosstalk corrections determined in block 303 are applied to the spatially corrected ensemble of images in a block 306. It is important that the spatial corrections be applied before the spectral corrections are applied. The spatially and spectrally corrected ensemble of images is available as data output at a block 307.

Note that during image processing (in blocks 304–307), the spatial and spectral computation algorithms represented by blocks 302 and 303, respectively, continue to produce measurements that indicate the stability or confidence of the corrections previously applied (with respect to the "live" calibration embodiment described above). Once the algorithm determines that such instability exists, the spatial and spectral calibrations can once again be performed, and the newly generated spatial and spectral correction factors can be applied to additional ensemble of images (until instability is detected, which will cause additional calibrations to be performed). The image processing stages (of blocks 304–307) can be applied in real time as images are collected during system operation, or offline, by accessing stored image files. The images of the image ensemble output in block 307 can be used for further processing and analysis, free of the information degradation caused by crosstalk between channels.

As noted above, stored data, rather than live data, can be used to provide, or augment, the required spatial and spectral correction factors. In addition to stored data derived from a calibration image as described above, other types, of stored data can be used to provide additional correction factors. Such data can include stored tables of constants that are derived from measurements and from known characteristics of the objects being imaged. As noted in a block 308, the general positions or channel start columns for the images produced by an instrument such as that shown in FIG. 1B, and inverted source coefficients, as indicated in a block 309, comprise stored information that can be used as correction factors. Such stored constants are not derived from a calibration image.

Figure 4:
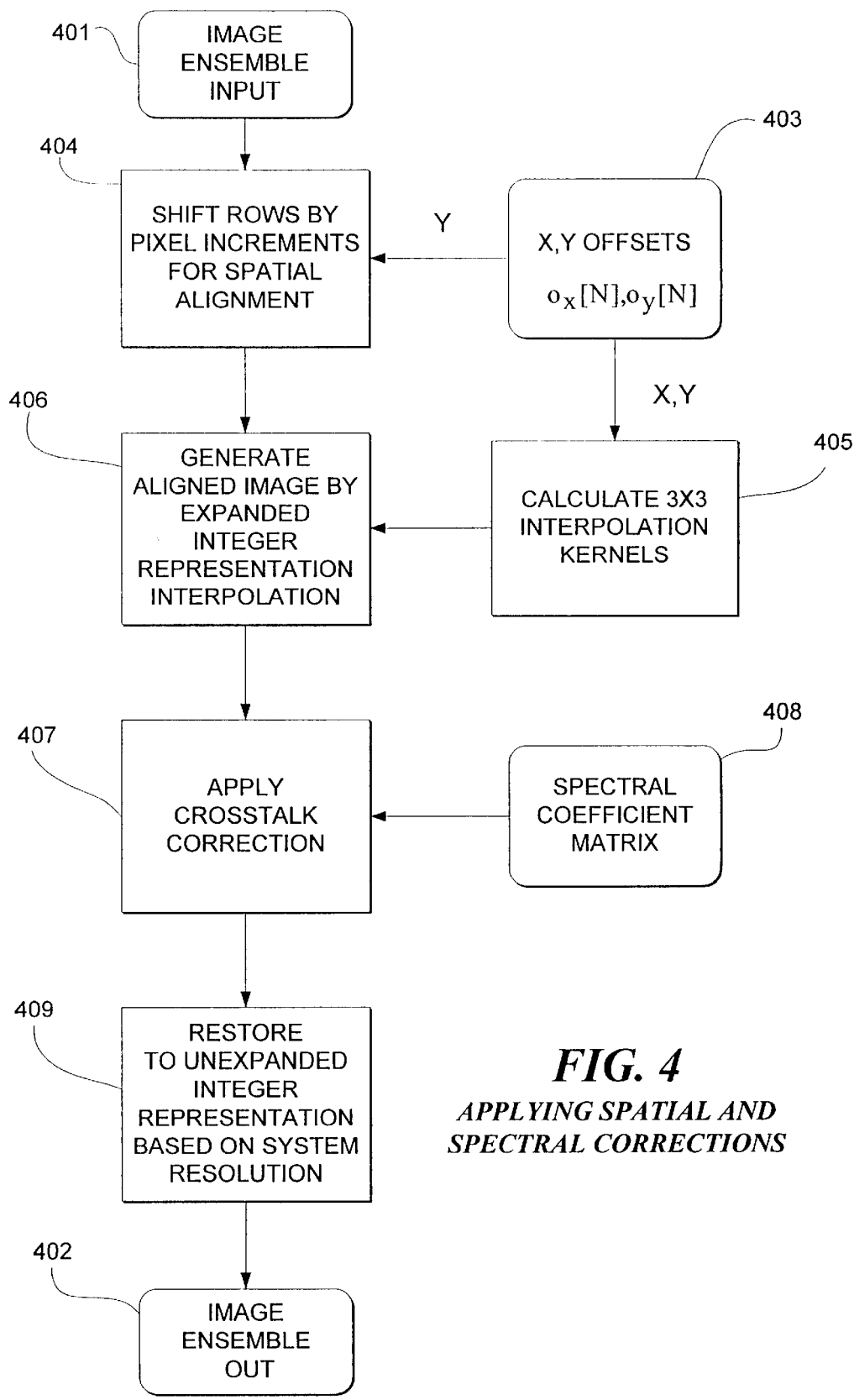
FIG. 4 is a flow chart showing the logical steps in applying spatial and spectral corrections to image signals, in accord with the present invention.
Figure 10:
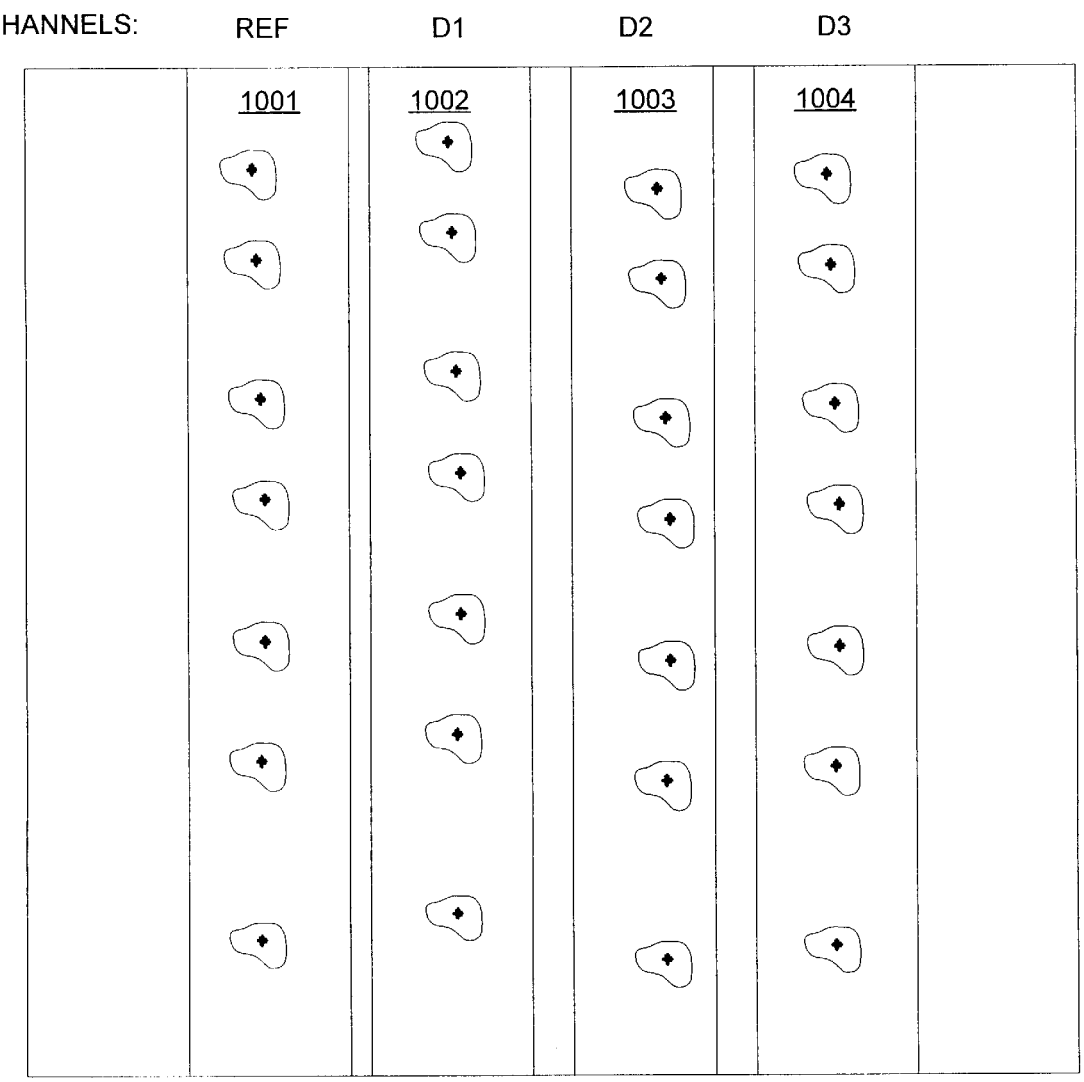
FIG. 10 is a schematic diagram depicting three data images and one reference image of objects in a flow stream, showing the objects as misaligned.

A flow chart of the general operations of an embodiment of the present invention is shown in FIG. 4. An image ensemble input in a block 401 is the composite signal for a set of images, all of which depict the same field of view, but each of which has been constructed using a signal from a different channel. The number of images in an ensemble is thus equal to the number of channels in the instrument. For example, an image ensemble in which there are four channels is represented in FIG. 10. The reference channel can be any of the channels, although in one preferred embodiment, a bright field channel is preferred over fluorescence channels for use as the reference channel. Referring to FIG. 10, for illustration purposes, the leftmost (first) channel is the reference channel. The first image ensemble would thus include the first cell image from each channel; the second image ensemble would include the second cell image from each channel; and the Nth image ensemble would include the Nth cell image from each channel.

The x (horizontal) and y (vertical) offsets 403 must be established in order for the alignment process to operate on the image ensemble. As noted above in regard to block 301 of FIG. 3, the calibration image is processed to compute spatial X,Y offsets, determining offset values that are input in a block 403 of FIG. 4. The calibration process may be run as a preliminary step in the operation of the instrument and is preferably repeated periodically to accommodate any drift in the image registration caused, for example, by changes in temperature. Details of the process for generating the offsets are illustrated in the flow chart of FIG. 6.

In a block 404, the signals are aligned by selecting one signal in the image ensemble as a reference image and shifting each other signal in the image ensemble by pixel increments to align as closely as possible to the reference signal. Note that shifting by whole pixel increments will rarely fully align the signals, so other steps are needed. For each of the non reference signals, a 3×3 interpolation kernel is calculated in a block 405. The interpolation process is described in more detail below, particularly with respect to FIG. 14.

Each non reference signal in the image ensemble is further aligned in a block 406 to a fraction of a pixel by interpolation where the aligned image is represented by expanded integer representation. Expanding the integer representation of the image data to a larger number of bits than the resolution of the captured image enables faster processing to be achieved. This step is particularly important in embodiments that generate spatial correction data "live." In a preferred embodiment of the present invention, the image is originally captured with a resolution of 8-bits, and in block 406, the data are expanded to 16-bits or 32-bits, for ease of processing. This step helps prevent the introduction of round-off errors encountered when processing integers having fewer bits.

Once each signal in the image ensemble is aligned, in a block 407 the crosstalk correction is applied, using a spectral coefficient matrix from a block 408. The crosstalk correction is described in greater detail below. In a block 409, the expanded integer representation is returned to the unexpanded integer representation corresponding to the resolution of the system. The purpose of the return to the unexpanded representation is to reduce the memory required to store the processed image data. In at least one embodiment, the unexpanded representation is an 8-bit digital gray-scale. In a block 402, the signals of the image ensemble have been aligned and crosstalk among the signals has been reduced, and the processing of the image ensemble is complete.

Spatial Alignment

Figure 5:
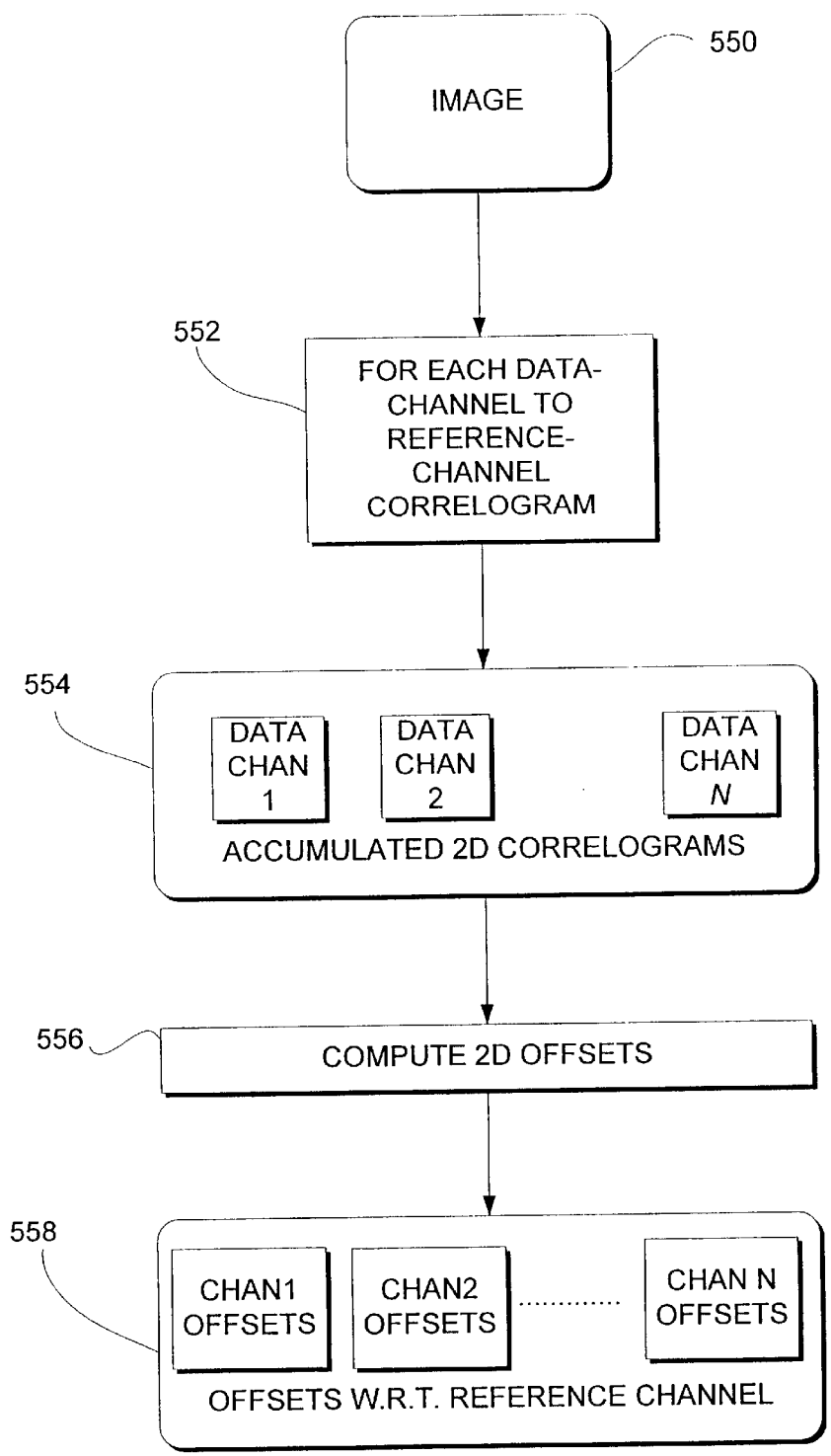
FIG. 5 is a flow chart showing the logical steps in the calibration phase of spatial corrections to image signals, in accord with the present invention.

FIG. 5 summarizes the spatial calibration stage. A block 550 represents a sequence of image ensembles. A single image ensemble produces a correlogram ensemble, where each correlogram corresponds to a non-reference channel convolved with the reference channel; this convolution is performed in a block 552. The correlogram ensemble generated from a single image ensemble may not accurately convey the image offsets, especially if those images contain only a few objects. The accuracy and signal-to-noise ratio of the correlogram ensemble can be enhanced by producing correlogram ensembles on a sequence of image ensembles. These correlogram ensembles are accumulated by the N non-reference channels in a block 554. Also in block 554, the accumulated correlograms are used to generate a single correlogram ensemble that represents the average of the sequence of correlogram ensembles.

When the sequence of image ensembles have been processed, the exact peaks of the accumulated correlogram ensemble are located by computing the two-dimensional offsets in a block 556, and the coordinates of the peaks are stored as the x and y offsets in a block 558. Since objects may occupy only a few pixels, and because the resolution of the imaging system may be on the order of a pixel width, alignment of one image to the next, to a resolution of a fraction of a pixel width is necessary for accurate crosstalk correction. The true peak of the correlogram will rarely be centered on a pixel, but can be located by analyzing the shape of the region around the pixel of maximum amplitude. By defining an accurate equation for the correlogram amplitude in that region, the true location of the peak can be determined to a resolution that is a fraction of a single pixel dimension. Therefore, the offset information stored in block 158 consists of x and y offsets that are in units of fractions of pixels. Then, an appropriate reconstruction filter is applied to compute pixel values for the fractional offsets.

In summary, the spatial calibration process involves producing an averaged correlogram ensemble and then computing the peak of the average correlogram to within a fraction of a pixel position. Further details relating to blocks 552 (Correlogram Ensemble) and 556 (Offset Determination) are provided below.

Correlogram Ensemble

Figure 6:
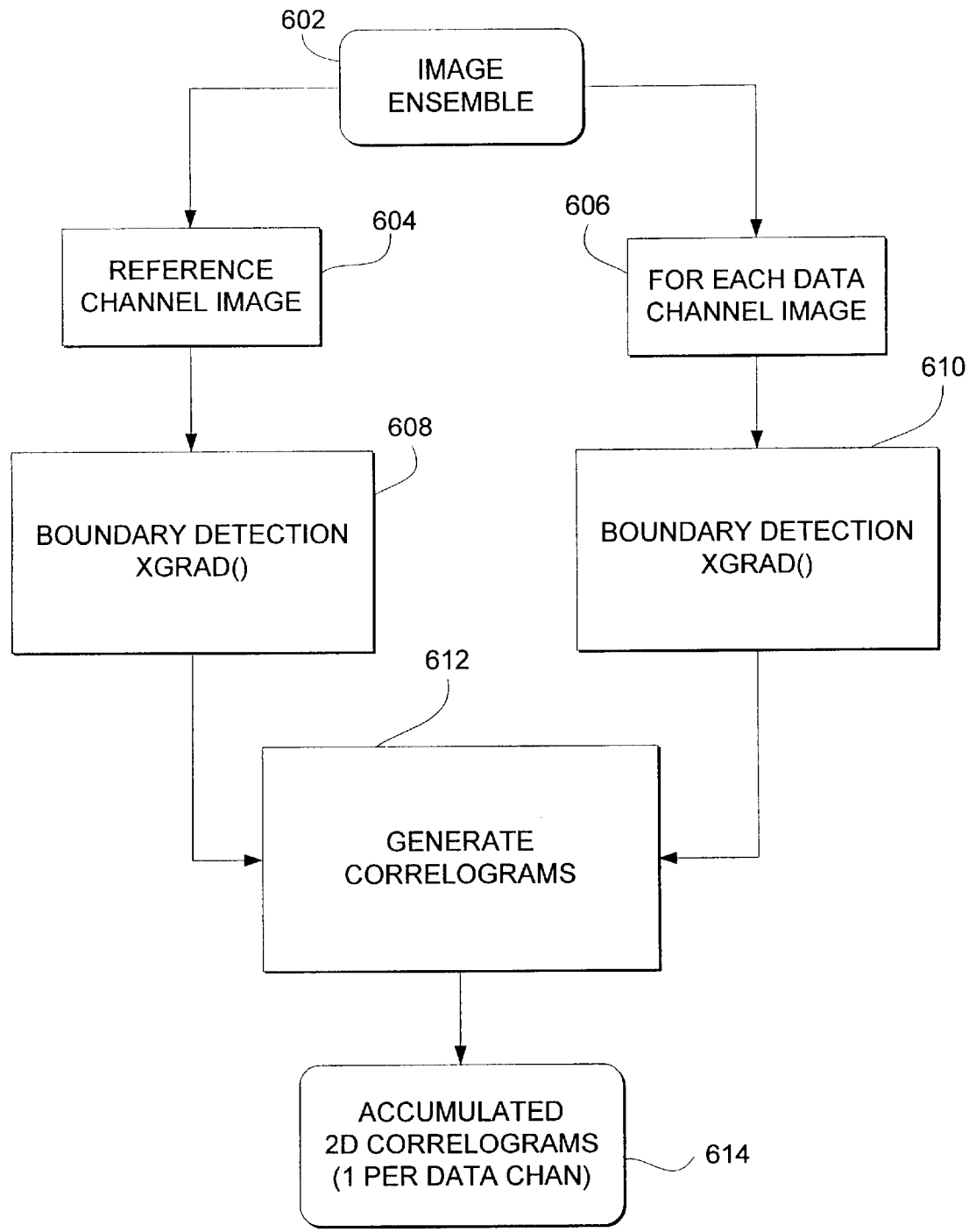
FIG. 6 is a flow chart showing the steps employed for generating accumulated average correlograms between the data images and the reference image.

FIG. 6 refers to the steps employed for computing the correlogram ensemble. A block 602 represents the image ensemble input, and a block 604 represents the reference image from the image ensemble. A block 606 represents each non-reference data channel image. In a block 608, the reference image of block 604 is processed through a boundary enhancement algorithm. The non-reference data channel images of block 606 are also processed through the boundary image enhancement algorithm in a block 610. The boundary enhanced data from blocks 608 and 610 are used to generate a correlogram in a block 612. The completed correlograms are accumulated in a block 614, until a correlogram has been generated for each data channel with the reference data channel. As described in more detail below, several methods can be employed to generate the correlograms, including manipulating the signals in the frequency domain or in the spatial domain.

The boundary image enhancement performed in blocks 608 and 610 is achieved by using a two-dimensional gradient operator to suppress flat surfaces and to enhance object boundaries to better facilitate boundary detection. The operator builds signal in regions where the slope of the intensity is large in both the vertical and the horizontal directions. The linear expression for this operator is as follows:

$$G = \frac{\partial}{\partial y} \frac{\partial I}{\partial x}. \tag{2}$$

A preferred implementation of the gradient operator in sampled image space is as follows:

$$G_{i,j} = |(I_{i+1,j+1} - I_{i-1,j+1}) - (I_{i+1,j-1} - I_{i-1,j-1})|. \tag{3}$$

Figure 7:
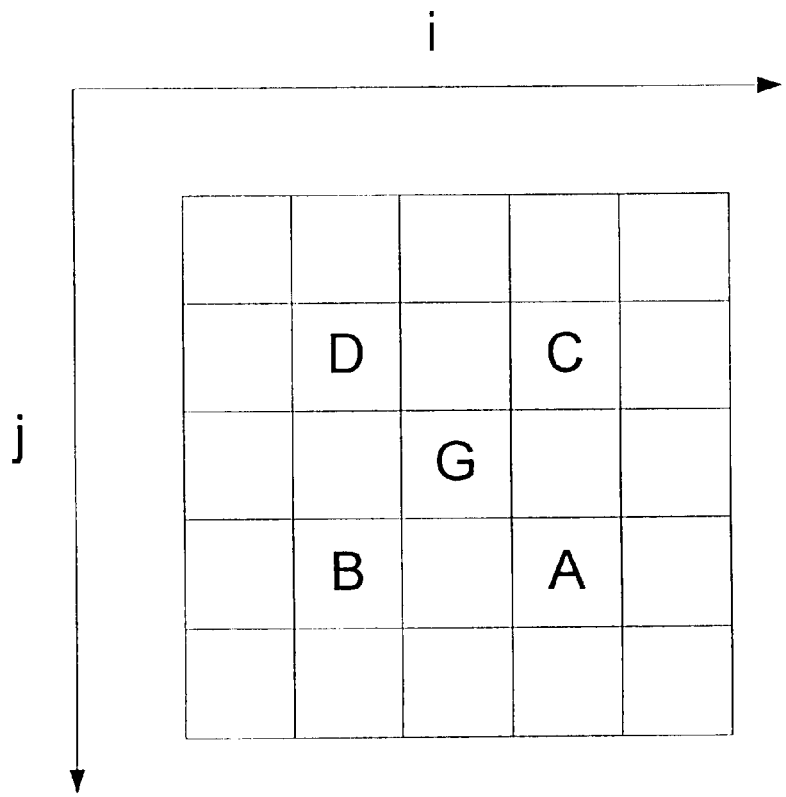
FIG. 7 is a schematic diagram indicating the locations of pixels used in determining the correlogram gradient operator, and an equation for that operator.
Figure 8:
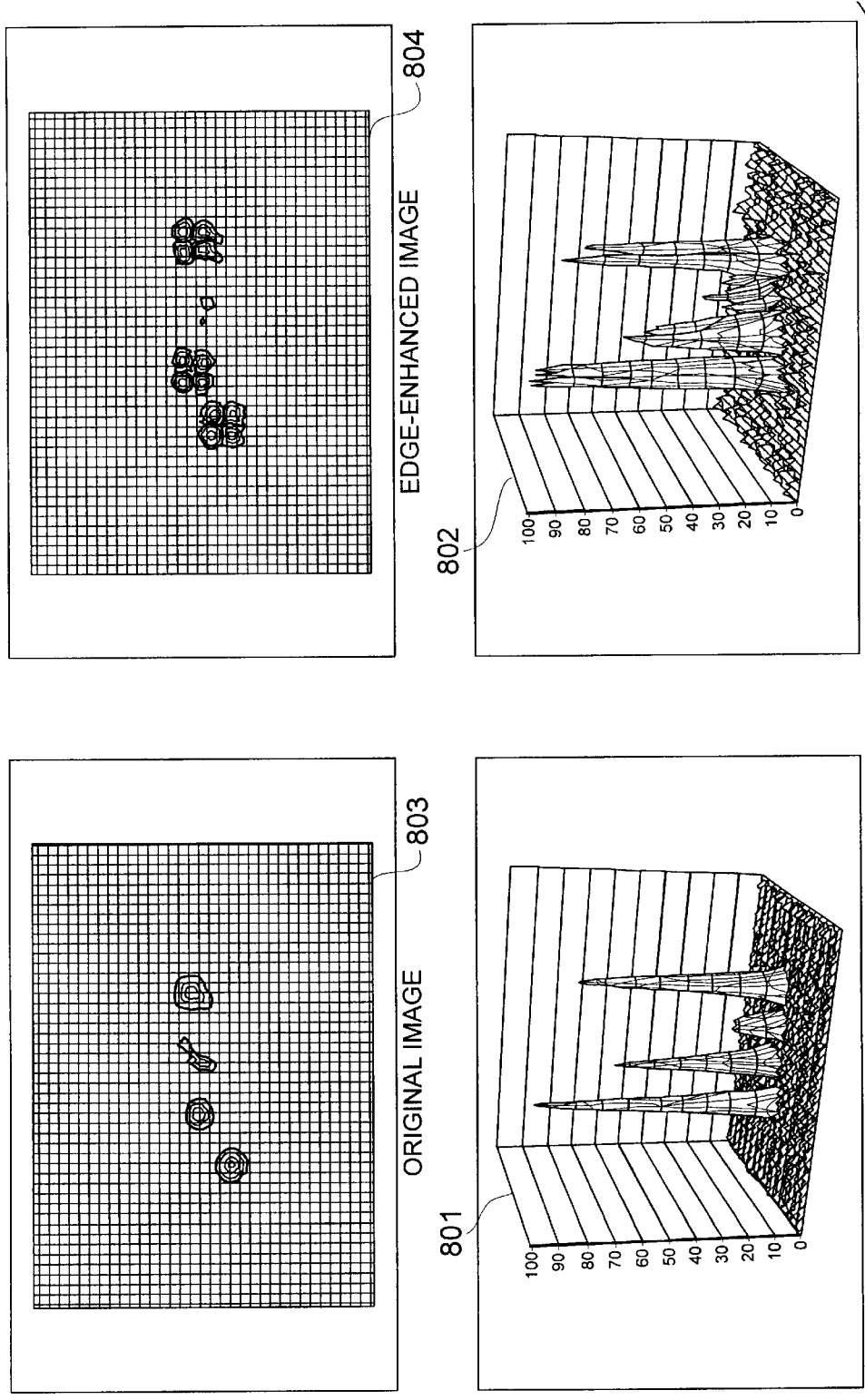
FIG. 8 illustrates two surface plots and two contour plots of a subregion of an image, including one surface plot and one contour plot before, and one surface plot and one contour plot after application of the correlogram gradient operator.

This operation is illustrated in FIG. 7. For each pixel in the image, the gradient is computed from the adjacent pixels, in the diagonal directions. The effect of this gradient operator is illustrated in FIG. 8. Surface plots 801 and 802 and contour maps 803 and 804 are shown for an image before and after transformation by the gradient operator. The operator transforms each Gaussian curve for an image into a cluster of four sharp peaks and is effective for images with either positive or negative contrast.

Object boundaries carry all of the energy in the images transformed by the gradient operator. It is then necessary to effectively overlay each data image onto the reference image and measure the vertical shift and horizontal shift required to align object boundaries. Cross-correlation is a preferred method for measuring these shifts, or offsets, between the reference and data images. As noted above, once the boundary data have been generated, the correlogram is produced. The cross-correlation of two signals (s1 and s2), where one signal is a mirror of itself, is determined by convolving the two signals, producing a correlogram. The convolution operation in the spatial domain is defined by the following equation:

$$f_1(x,y) \otimes f_2(x,y) = \int\int_{-\infty}^{\infty} f_1(\varepsilon, \eta) f_2(x-\varepsilon, y-\eta) d\varepsilon d\eta. \tag{5}$$

Choosing the first function to represent the first signal, or f1(t)=s1(t), and the second function as the mirror of the second signal, or f2(t)=s2(−t), Equation (4) represents a correlogram in one dimension. The value of the convolution for every time sample, t, is the sum over infinity of the product of the two functions, but with the second function offset by a time delay t. The time delay between the two signals can be determined by finding the peaks in the correlogram. For image realignment, the convolution is applied in two dimensions to functions in x, y space, as follows:

$$f_1(t) \otimes f_2(t) = \int_{-\infty}^{\infty} f_1(\lambda) f_2(t-\lambda) d\lambda. \tag{4}$$

For a two dimensional correlogram, let $f_1(x,y) = s_1(x,y)$ and $f_2(x,y) = s_2(-x,-y)$. The alignment method is based on the premise that there will be similar structures in the images to be aligned. In the ideal case, the second image is identical to the first except for a shift in x and y. Furthermore, the shift can be represented as the convolution of the function with the two-dimensional Dirac delta function:

$$f_2(x,y) = f_1(x-x_0, y-y_0),$$

and $$f_2(x,y) = f_1(x,y) \otimes \delta(x-x_0, y-y_0). \tag{6}$$

The image offsets, $x_0$ and $y_0$, can be measured from the shift in the two-dimensional correlogram, since:

$$C_{1,2} = f_1(x,y) \otimes f_2(x,y) = f_1(x,y) \otimes f_1(x,y) \otimes \delta(x-x_0, y-y_0) \tag{7}$$

The Fourier Transform provides a convenient method for accomplishing the convolution of two images, as evident from the relationship:

$$f_1(x,y) \otimes f_2(x,y) = F^{-1}[F_1(\omega_x,\omega_y) \cdot F_2(\omega_x,\omega_y)], \tag{8}$$

where $F(\omega_x,\omega_y)$ is the Fourier Transform of $f(x, y)$, and $F^{-1}[X(\omega_x,\omega_y)]$ is the Inverse Fourier Transform of $X(\omega_x,\omega_y)$. The mirror of a function has the following relationship between spatial domain and frequency domain representations:

$$F_2(w_x, w_y) = \overline{S_2(w_x, w_y)} = F[s_2(-x,-y)]$$

where the overbar is the complex conjugation and $S(w_x, w_y)$ is the Fourier Transform of $s(x, y)$.

In the frequency domain, the two-dimensional convolution becomes an element-by-element multiplication of the spectra of the two images. Therefore, a two-dimensional correlogram is obtained by performing an inverse Fourier Transform on an element-by-element multiplication of the Fourier Transform on one signal and the Fourier Transform on the mirror of the other signal. It should be noted that Equations 5–7 apply both to manipulations in the frequency domain and the spatial domain, whereas Equation 8 applies only to manipulations in the frequency domain.

Figure 9:
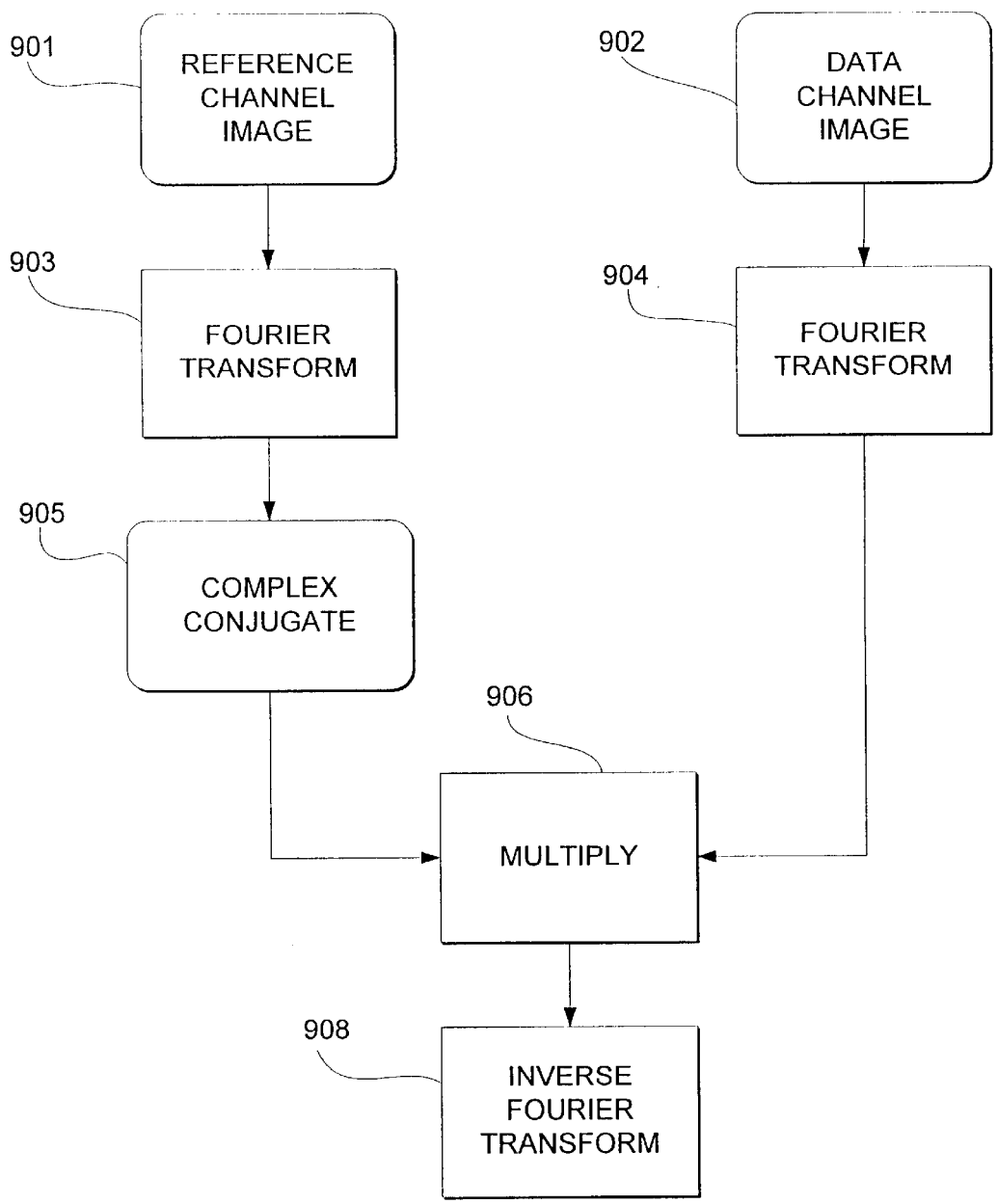
FIG. 9 is flow chart showing the steps for computing the correlogram between a data image and a reference image in the frequency domain.

In FIG. 9 are illustrated the steps for implementing the cross correlation process performed as a multiplication in the frequency domain. Two images from the image ensemble are input to this process. The first image is a reference image, as indicated in a block 901, and is from the channel that is designated as the reference channel for the alignment. FIG. 10 depicts a four-channel system with a reference channel 901. The other three channels 1002, 1003, and 1004 are data channels. Preferably, channel 1001 corresponds to a bright field image, while channels 1002–1003 correspond to fluoresced images. As explained below in further detail, the images from the data channels are transformed to align vertically—as shown (i.e., in time) with the corresponding images from the reference channel.

Referring again to FIG. 9, a complex Fourier Transform is applied to both reference and data images in blocks 903 and 904, respectively. The output of the Fourier Transform is a matrix of complex numbers representing the amplitude and phase of each frequency in the base set. Before multiplication of the two spectra, a conjugation operation is applied to the spectrum of the reference image in a block 905. The complex conjugate of the spectrum of the reference image is multiplied by the spectrum of the data image in a block 906. Finally, an inverse Fourier Transform is applied to the product in a block 908, which produces the two-dimensional correlogram.

While the process described above for preparing a two-dimensional correlogram in the frequency domain is effective, manipulating the signal data in the frequency domain is likely to be more computationally expensive than preparing a correlogram by manipulating the signal data in the spatial domain. The full range of offsets are computed in the frequency domain, while knowledge about the sample set can be imputed to limit the range of offsets computed in the spatial domain, as described above in conjunction with FIG. 6.

The computation of the correlogram in block 612 of FIG. 6 may be performed either in the spatial domain or the frequency domain. If the relative spatial alignment cannot be restricted by prior knowledge, then the frequency domain is preferred for the sake of computational efficiency. If, on the other hand, prior knowledge restricts the possible alignments of the image channels to a relatively small range of positions, then it is more computationally efficient to compute the correlograms in the spatial domain.

In practice, it is likely that an instrument embodying the present invention would use the frequency domain method of computation during a system set-up or qualification step, after which, the channel alignments would be fixed to a small range of possible positions, so that any adjustments to the channel alignments for a given image ensemble would be calculated in the spatial domain over this restricted range. FIG. 9, as discussed above, describes the calculation of the correlogram in the frequency domain. The following discussion describes the calculation of the correlogram in the spatial domain.

As shown in FIG. 6, the calculation of the correlogram (regardless of whether the calculation is in the frequency domain or in the spatial domain) uses two image inputs, one input (in block 604 of FIG. 6) corresponding to the reference channel, and the other input (in block 606 of FIG. 6) corresponding to another data channel. Assign a label of $R_{ij}$ to the input data from the reference channel, and $S_{ij}$ to the input data from the other channel, where i and j are spatial indices having integer values within the domain of each channel. For definiteness, assume that in the current computation, i takes on values in the range [0, m−1] and j takes on values in the range [0, n−1]. The correlogram value $C_{a,b}$ is computed as a function of integer offsets a and b, by the following formula:

$$C_{a,b} = \sum_{i=0}^{m-1} \sum_{j=0}^{n-1} R_{i,j} S_{(i+a) \bmod m, (j+b) \bmod n}$$

where p mod q is the remainder when p is divided by q. When the maximum of the correlogram $C_{a,b}$ is known to occur somewhere in a relatively small range of values of the offsets a and b, this formula may provide the most efficient computation of the correlogram available. If, on the other hand, the values $C_{a,b}$ for the full range of possible offsets a and b must be computed, the computation in the frequency domain is much more efficient.

Figure 11:
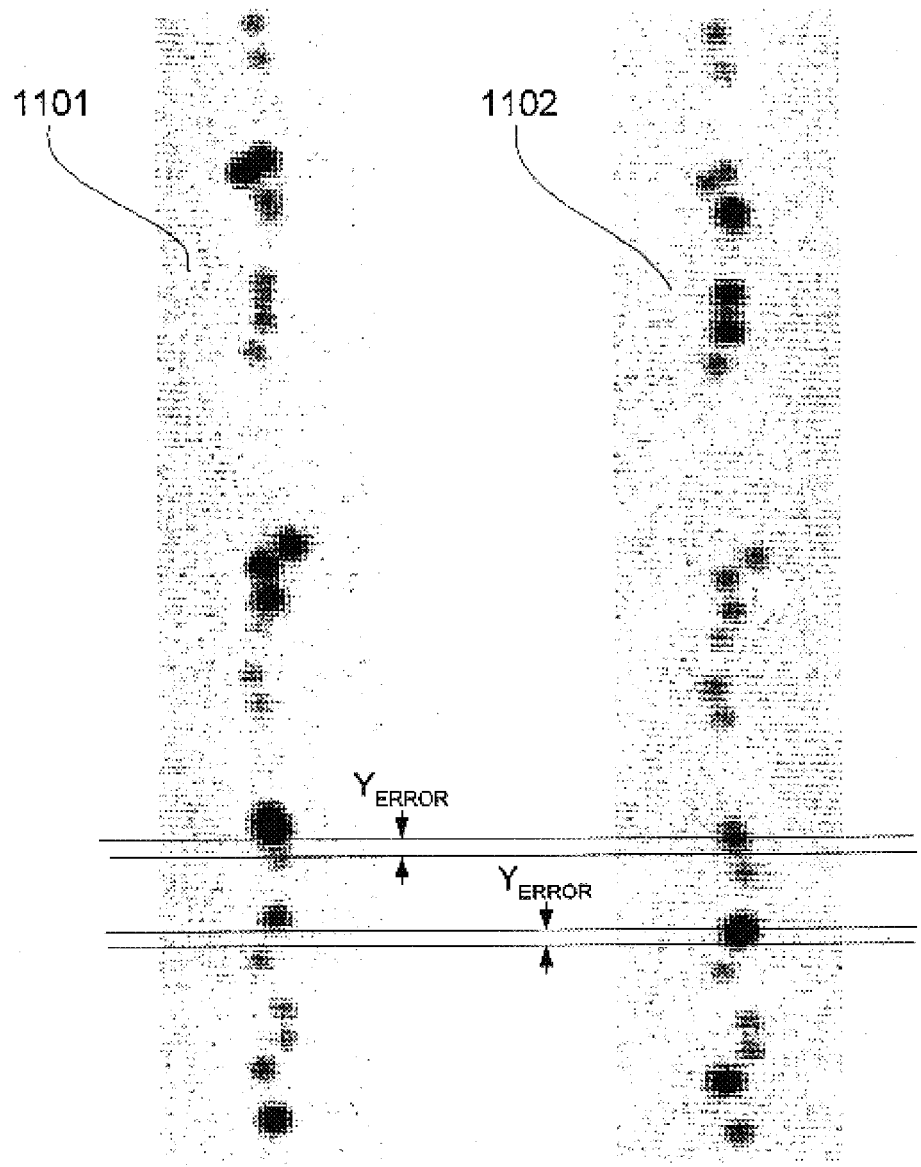
FIG. 11 illustrates two grayscale images for two channels of a flow imaging instrument, indicating a vertical misalignment between the two channels.
Figure 12:
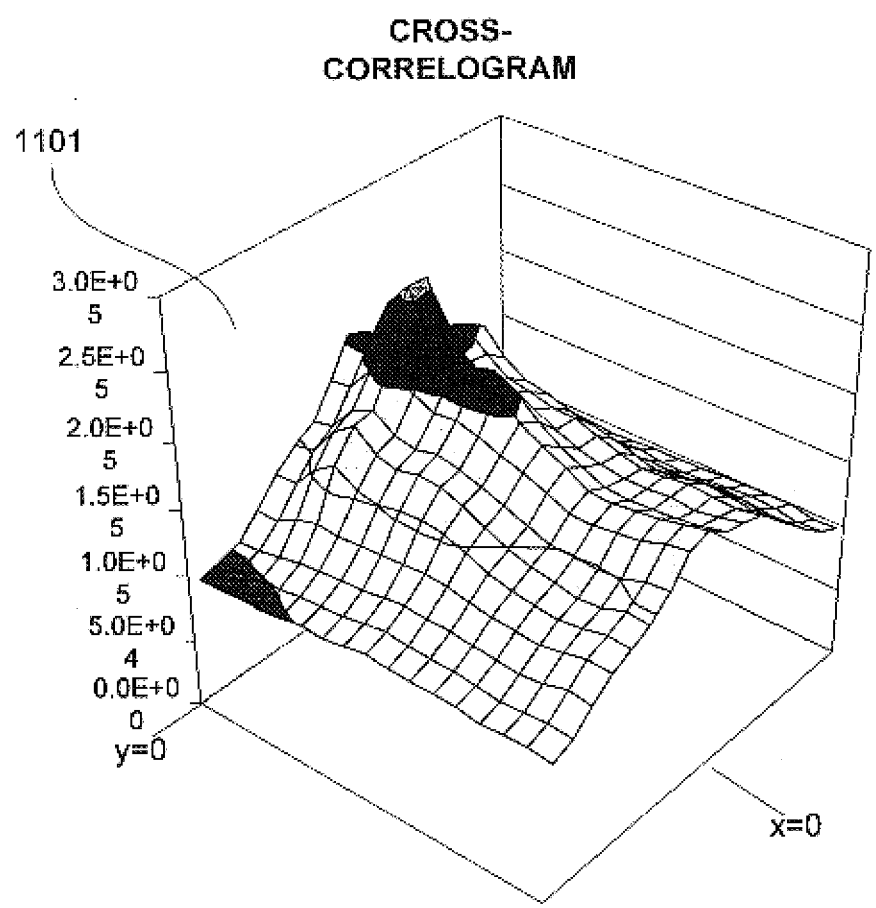
FIG. 12 is a surface plot of the cross-correlogram for the two images shown in FIG. 11.

FIG. 11 shows two images 1101 and 1102 for two sets of objects. The second set of objects in image 1102 is shifted along the Y axis (vertically—as shown) by an amount, $Y_{error}$, relative to the first set of objects. FIG. 12 includes a surface plot 1201 of the correlogram generated using the process steps indicated in FIG. 9. Note that for perfect alignment of the two images, the peak of the correlogram would be a single point at the origin of the plot.

Offset Determination

Figure 13:
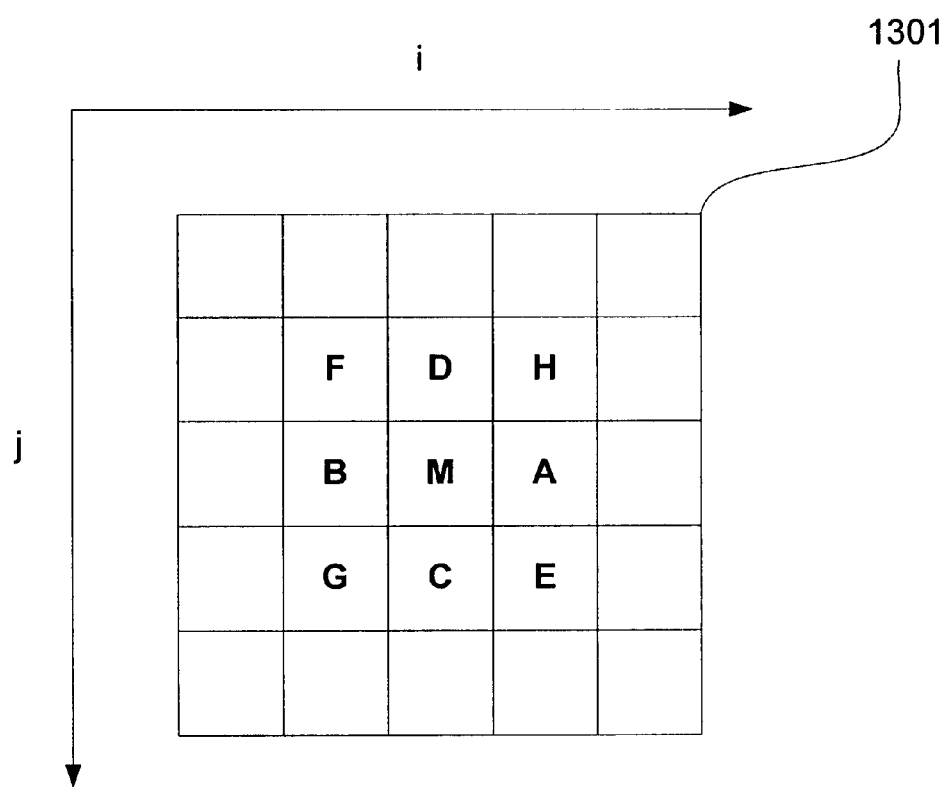
FIG. 13 is a schematic diagram illustrating the relative locations and letter designations of pixels used in the computation of surface derivatives for locating a peak of a correlogram.

In the present invention, the correlogram peak region is described by a second-order Taylor series expansion constructed from locally measured first- and second-order derivatives. As an example, nine pixels centered on a peak pixel, M, can be used to compute six derivatives. Referring to FIG. 13 for pixel locations 1301, the equations for these derivatives are as follows:

$dx = (A-B)/2$ $dy = (C-D)/2$ $d^2x = A+B-2\text{Max}$ $d^2y = C+D-2\text{Max}$ $dydx = dxdy = (E+F-G-H)/4$ (9)

These terms consist of the first and second derivatives of the amplitude in the x and y directions and two terms that are more explicitly described by partial derivatives as follows:

$$dydx = \frac{\partial}{\partial y}\left(\frac{\partial A}{\partial x}\right) \qquad (10)$$

and $$dxdy = \frac{\partial}{\partial x}\left(\frac{\partial A}{\partial y}\right)$$

A matrix is constructed of the second-order derivatives as follows:

$$A = \begin{bmatrix} d^2x & dydx \\ dxdy & d^2y \end{bmatrix}. \qquad (11)$$

The surface around the correlogram peak is then described by the Taylor series expansion:

$$C = C_0 + \vec{d} \cdot \vec{p} + 0.5 \vec{p} \cdot A \cdot \vec{p} \qquad (12)$$

where "•" is the Euclidian inner or dot product, $\vec{p}$ is the vector from a peak pixel center to a true maximum, $\vec{d}$ is a vector of first derivatives, A is a matrix of second order derivatives, and $C_0$ is the correlogram bias. The peak of the correlogram surface is identified as that location at which the gradient of the amplitude goes to zero, which corresponds to the following condition:

$\text{Grad}(C) = \vec{d} + A \cdot \vec{p} = 0$ or:

$$\vec{p} = A^{-1} \cdot \vec{d} \qquad (13)$$

The two terms dxdy and dydx in matrix A are computationally identical. Therefore, A is symmetrical and orthogonally diagonalizable. The inverse of matrix A can therefore be conveniently found by computing the eigenvalues and eigenvectors of A and applying the following equivalence:

$$A = e^t D e \qquad (14)$$

$$= \begin{bmatrix} e_{11} & e_{12} \\ e_{21} & e_{22} \end{bmatrix} \begin{bmatrix} \lambda_1 & 0 \\ 0 & \lambda_2 \end{bmatrix} \begin{bmatrix} e_{11} & e_{21} \\ e_{12} & e_{22} \end{bmatrix}$$

where e in the first of the above equations is the eigenvector matrix of A, and D equals the eigenvalue matrix of A. Similarly, the inverse of A is:

$$A^{-1} = e^t D^{-1} e \qquad (15)$$

$$= \begin{bmatrix} e_{11} & e_{12} \\ e_{21} & e_{22} \end{bmatrix} \begin{bmatrix} \frac{1}{\lambda_1} & 0 \\ 0 & \frac{1}{\lambda_2} \end{bmatrix} \begin{bmatrix} e_{11} & e_{21} \\ e_{12} & e_{22} \end{bmatrix}$$

The inverse eigenvalue matrix $D^{-1}$ can be used in place of $A^{-1}$, if the derivative vector is rotated into the eigenvector coordinate system. The rotated version of the misalignment vector is as follows:

$$\vec{p}' = \frac{1}{\lambda}\vec{d} \cdot \vec{e}. \quad (16)$$

Finally, the misalignment vector is rotated back into the image x, y coordinate system by application of the transpose of the eigenvector matrix, as follows:

$$\vec{p} = \vec{p}' \cdot \vec{e}^t. \quad (17)$$

The x offset $o_x$ and y offset $o_y$ to be applied to the data image to realign it with the reference image are then determined as follows:

$$o_x = i_{max} + p_x$$

and $$o_y = j_{max} + p_y \quad (18)$$

where $i_{max}$, $j_{max}$ is the offset of the correlogram peak from the origin, and $p_x$, $p_y$ corresponds to the projection of $\vec{p}$ onto the x and y axes.

Typically, $o_x$ and $o_y$ are not integral multiples of pixels. Therefore, the data image cannot simply be shifted by a certain number of pixels for alignment to the reference image. Instead, the data image is aligned to the nearest pixel and then the content of the data image is reconstructed by interpolation to a fraction of a pixel. The result of this second operation closely approximates the amplitude values that would have been captured had there been no misalignment.

In the present invention, an image is reconstructed for alignment by application of a two-dimensional interpolation. In this process, once the image has been aligned with the reference image to the nearest pixel, the new amplitude value for each pixel is computed as the weighted sum of a group of surrounding pixels. The values of the weighting coefficients for the interpolation depend on the extent of fractional pixel shifting that must be accomplished in the vertical and horizontal directions.

Figure 14:
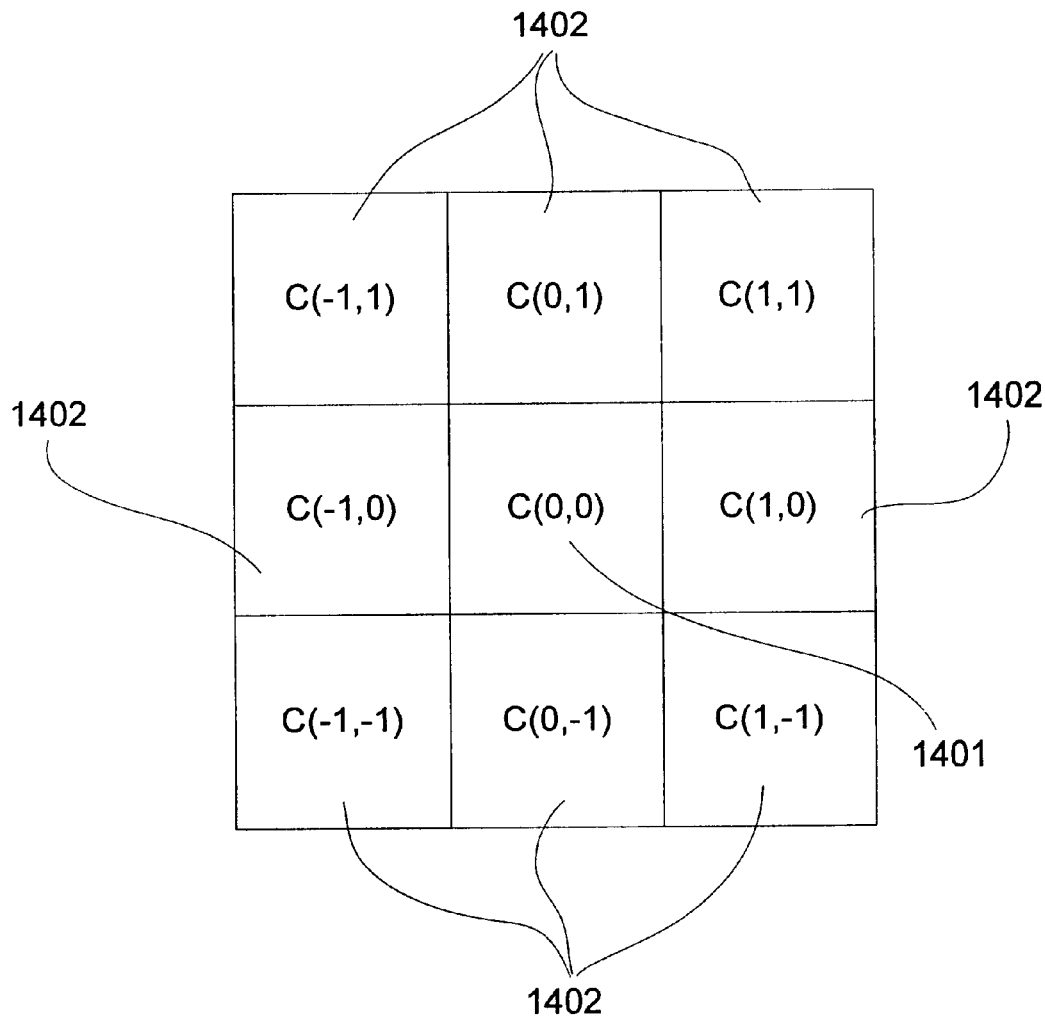
FIG. 14 is a schematic diagram depicting the relative pixel locations and variable names of the coefficients used in a two-dimensional interpolation for reconstructing the data images.

For example, a new pixel value might be computed from a group of nine pixels as shown in FIG. 14. The center pixel is taken as the origin, and the shift offsets, $o_x$ and $o_y$, define the desired new location for the center pixel. A pixel that is far from the new location will have a small value for its interpolation coefficient. A pixel that is very close to the desired location will have a large value for its interpolation coefficient.

In the preferred embodiment of the present invention, coefficients 1401 and 1402 shown in FIG. 14 are related to the offsets, $o_x$ and $o_y$, through the following equations, which are derived from a Taylor expansion model of the source intensity:

$$c(0, 0) = 1 - o_x^2 - o_y^2, \quad (19)$$

$$c(-1, 1) = c(1, -1) = -\frac{o_x o_y}{4},$$

$$c(1, 1) = c(-1, -1) = \frac{o_x o_y}{4},$$

$$c(0, 1) = \frac{o_y(o_y - 1)}{2},$$

$$c(0, -1) = \frac{o_y(o_y + 1)}{2},$$

$$c(-1, 0) = \frac{o_x(o_x - 1)}{2}, \text{ and}$$

$$c(1, 0) = \frac{o_x(o_x + 1)}{2}$$

Figure 15:
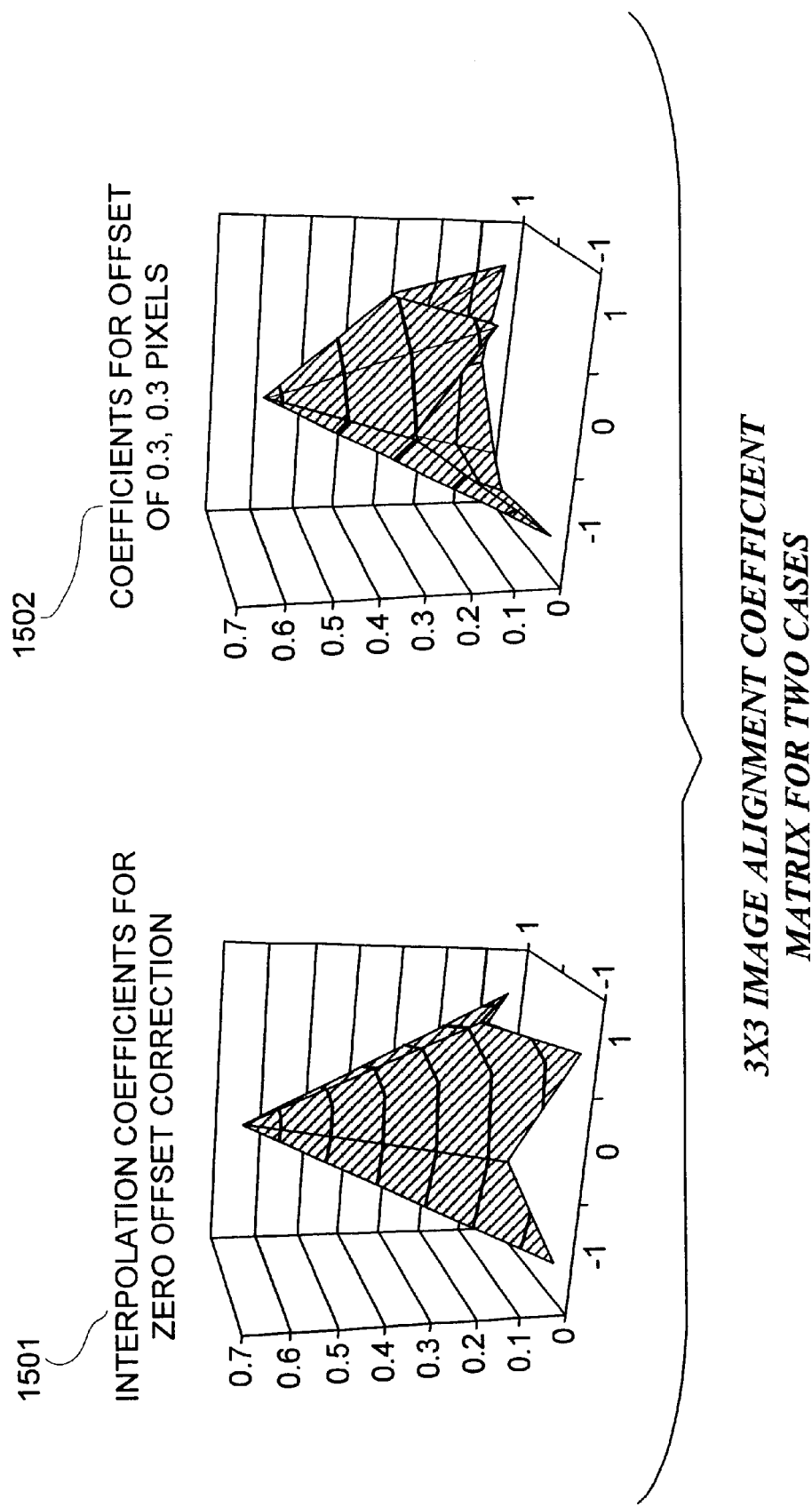
FIG. 15 illustrates surface plots of the interpolation coefficients for two pairs of image alignment offsets, including a zero offset correction and an offset of 0.3 pixels (each axis)

FIG. 15 shows surface plots of the interpolation coefficient matrices produced by the preceding system of equations for two pairs of offset values, including an offset of zero (shown in a first surface plot 1501), and an offset of (0.3, 0.3) (shown in a second surface plot 1502). With the true correlogram peak exactly aligned to the center pixel in the 3×3 region, as in first surface plot 1501, the coefficient matrix is symmetrical about the center pixel. With the true peak residing at (0.3, 0.3) in second surface plot 1502, the coefficients are greater for the pixels nearest the true peak and less for the pixels far from the true peak.

The construction of the new, aligned data image is accomplished by applying these coefficients to each pixel using the following equation:

$$m'(i, j) = \sum_{p=-1}^{1} \sum_{q=-1}^{1} c(p, q) m(i + p, j + q). \quad (20)$$

The coefficient matrix has the important property of summing to 1.0, independent of the location of the true peak relative to the pixel grid. If the system of equations for computing the interpolation coefficients did not have this property, the value of m'(i,j) would depend on the offsets, $o_x$ and $o_y$, introducing inaccuracies in the image reconstruction for some offset values.

Crosstalk Correction

In FIG. 3, once the data images have been thus aligned in block 305, the crosstalk correction is carried out in block 306. The spatial corrections must be applied before the crosstalk corrections are applied to provide the maximum benefit. The emission spectrum plots of FIG. 2 exemplify a typical problem to be solved when correcting crosstalk. In a system involving fluorescent dyes and optical filters, the amplitudes of the measured signals for the three channels can be predicted from a set of equations, as follows:

$$m_1 = \alpha_{11} s_1 + \alpha_{12} s_2 + \alpha_{13} s_3$$

$$m_2 = \alpha_{21} s_1 + \alpha_{22} s_2 + \alpha_{23} s_3,$$

and $$m_3 = \alpha_{31} s_1 + \alpha_{32} s_2 + \alpha_{33} s_3 \quad (21)$$

where $m_i$ is the measurement from channel i, $s_j$ is the signal from source j, and $\alpha_{ij}$ is a weighting coefficient for source j into channel i.

The same system of equations can be expressed using matrix notation, as follows:

$$\vec{M} = A \vec{S} \quad (22)$$

where $\vec{M}$ is a vector of measurements, A is a coefficient matrix, and $\vec{S}$ is a vector of sources.

Preferably, the calibration process will be performed using objects (biological samples or synthetic beads) that only stimulate one of the spectral emission profiles (indicated by 201 within a single data channel). As noted above, such samples or beads are referred to as controls. It is also possible to calibrate the instrument using a batch of different samples, if at least some of the samples are controls. With respect to such controls, each stimulus corresponds to one of the signal inputs s1, s2, or s3. Thus, when image ensembles are produced, the images from each data channel will have a response (m1, m2, and m3) from a single stimulus (s1, s2, or s3). Using Equation (21), if one can determine that the sample with spectral emissions produced in response to the stimulus acting on the control (for example, stimulus s1) has produced the image ensemble, then coefficients from the first column of matrix A (Equation (22) are determined. Similarly, if one can determine that the sample with spectral emissions corresponding to stimulus N produced an image ensemble, then the Nth column of matrix A is determined. Given the measured response, the determination of the stimulus source can be inferred from the spectral emissions in FIG. 2. The stimulus from channel N will produce the largest measurement response in image data channel N. In other words, the pixel values will always be larger in the pixel from data channel N than the corresponding pixel location in other data channels. In the presence of noise, these measurements of the columns of A are averaged over many sample inputs so as to improve the signal-to-noise ratio of the measurements. A typical goal when using a multichannel imaging system is to find the values of vector S, since the S (source) values are usually related through some simple formula to important intrinsic characteristics of the target objects. For example, if S is the intensity of light emitted by fluorescent molecules in a cell, and each different fluorescent molecule is attached to a predetermined receptor protein molecule on the cell surface, then repeated measurements of S for a large collection of cells can be translated into an average number of receptor molecules per cell, which might well be a significant data point, e.g., in a biological experiment. Because of crosstalk, the M (measurement) values will not have a simple dependence on a single S value. However, techniques from linear algebra are available for solving the set of linear equations relating source values to measurement values.

The matrix form of the system of equations can be rearranged as follows:

$$\vec{S} = A^{-1}\vec{M}. \quad (23)$$

In this equation, the source values are generated from the measurements by matrix multiplication by the inverse of matrix A. The challenge is in finding that inverse.

The matrix A can reasonably be assumed to be square, since typically, one channel is dedicated to each source. However, this matrix cannot be assumed to be symmetrical. For that reason, the eigenvalue decomposition cannot be applied, and another method must be found for computing the inverse of A. Singular value decomposition is such a method. In this method, matrix A is expressed as the product of three matrices, as follows:

$$A = U^t \vec{D} V \quad (24)$$

where U, V equal row orthogonal matrices, $U^t$ equals a transpose of U, and $\vec{D}$ equals a vector of singular (diagonal) values of the matrix D.

Matrix D is the diagonal matrix (all off-diagonal components of D are zero) which results from the singular value decomposition of matrix A. The diagonal components of D are the "singular values" of the matrix A. Expressing an arbitrary matrix A in the form of Equation 24, where U and V are row orthonormal and D is diagonal, is referred to as "singular value decomposition." As those of ordinary skill in the art will recognize, using singular value decomposition readily facilitates the population of these three matrices.

Singular value decomposition is applied to reduce crosstalk works as follows. A vector M of measurements, and a vector S of the corresponding source intensities are employed. Hypothetically, M and S are related by Equation 22, where A is the crosstalk matrix. The values of A may be determined either by modeling the system or by an empirical set of measurements.

An important feature of this format for matrix A is that the inversion of matrix A is reduced to:

$$A^{-1} = V^t \vec{D}^{-1} U. \quad (25)$$

The inversion operations are straightforward, consisting of transposing matrix V and taking the inverse of the real number values of matrix D. With the new form of the inverse of the coefficient matrix, the equation for the source values can be expanded into a form useful for computation, as follows:

$$\vec{S} = A^{-1} \vec{M} \quad (26)$$
$$= V^t \vec{D}^{-1} U \vec{M}$$

Note that it is trivial to compute $\vec{D}^{-1}$ because D is a diagonal matrix, thus $\vec{D}^{-1}$ is merely the inverse of D. Note that M is the set of measurements generated by the imaging system, and that matrices V, D, and U are initially populated using the singular value decomposition described above. Thus, the source values S can be recovered, and crosstalk eliminated, from a set of measurements M by applying Equation 26.

It should be noted that there are computationally less expensive ways to compute the inverse of A. In a preferred embodiment, the aforementioned singular value decomposition method is employed because singular value decomposition can be performed in a manner that ensures numerical stability. For example, the term $\vec{D}^{-1}$ in Equation 25 is useful in determining this condition. The presence of some diagonal matrix elements of D that are relatively small is an indication that the inversion of A is not numerically stable. Specifically, such a condition indicates that there are one or more directions in source space, which are nearly degenerate in measurement space. Under such circumstances, it is contemplated that it will be useful either to inform the user that the measurements being made include a degeneracy that cannot be accurately resolved from the information provided, or that the relatively large values of $\vec{D}^{-1}$ (i.e., when values of D are relatively small, 1/D is relatively large) can be replaced with zero, to ignore the degenerate direction in the measurements.

Referring to Equation 26, the following three stages of computation are performed. First, multiplication of the measurement vector by the transpose of matrix V is implemented:

$$\begin{bmatrix} p_1 \\ p_2 \\ p_3 \end{bmatrix} = \begin{bmatrix} v^t_{11} & v^t_{12} & v^t_{13} \\ v^t_{21} & v^t_{22} & v^t_{23} \\ v^t_{31} & v^t_{32} & v^t_{33} \end{bmatrix} \begin{bmatrix} m_1 \\ m_2 \\ m_3 \end{bmatrix} \quad (27)$$

The "$m_x$" values are measurements from the signals, and the $v^t_x$ values are determined from matrix V, which is initially populated using the singular value decomposition described above.

Second, multiplication of the product vector by the inverse values of the singular values of matrix D is implemented:

$$q_1 = p_1 d_1^{-1}$$

$$q_2 = p_2 d_2^{-1}$$

$$q_3 = p_3 d_3^{-1} \quad (28)$$

where $d_i^{-1}$ is the inverse of element i of $\vec{D}$. Note that the "$p_x$" values are obtained from equation (27), and the $d_x^{-1}$ values are obtained from matrix D, which is initially populated using the singular value decomposition described above.

Third, multiplication by matrix U is implemented:

$$\begin{bmatrix} s_1 \\ s_2 \\ s_3 \end{bmatrix} = \begin{bmatrix} u_{11} & u_{12} & u_{13} \\ u_{21} & u_{22} & u_{23} \\ u_{31} & u_{32} & u_{33} \end{bmatrix} \begin{bmatrix} q_1 \\ q_2 \\ q_3 \end{bmatrix} \quad (29)$$

The "$q_x$" values are obtained from equation (28), and the $u_x$ values are obtained from matrix U, which is initially populated using the singular value decomposition described above.

Figure 16:
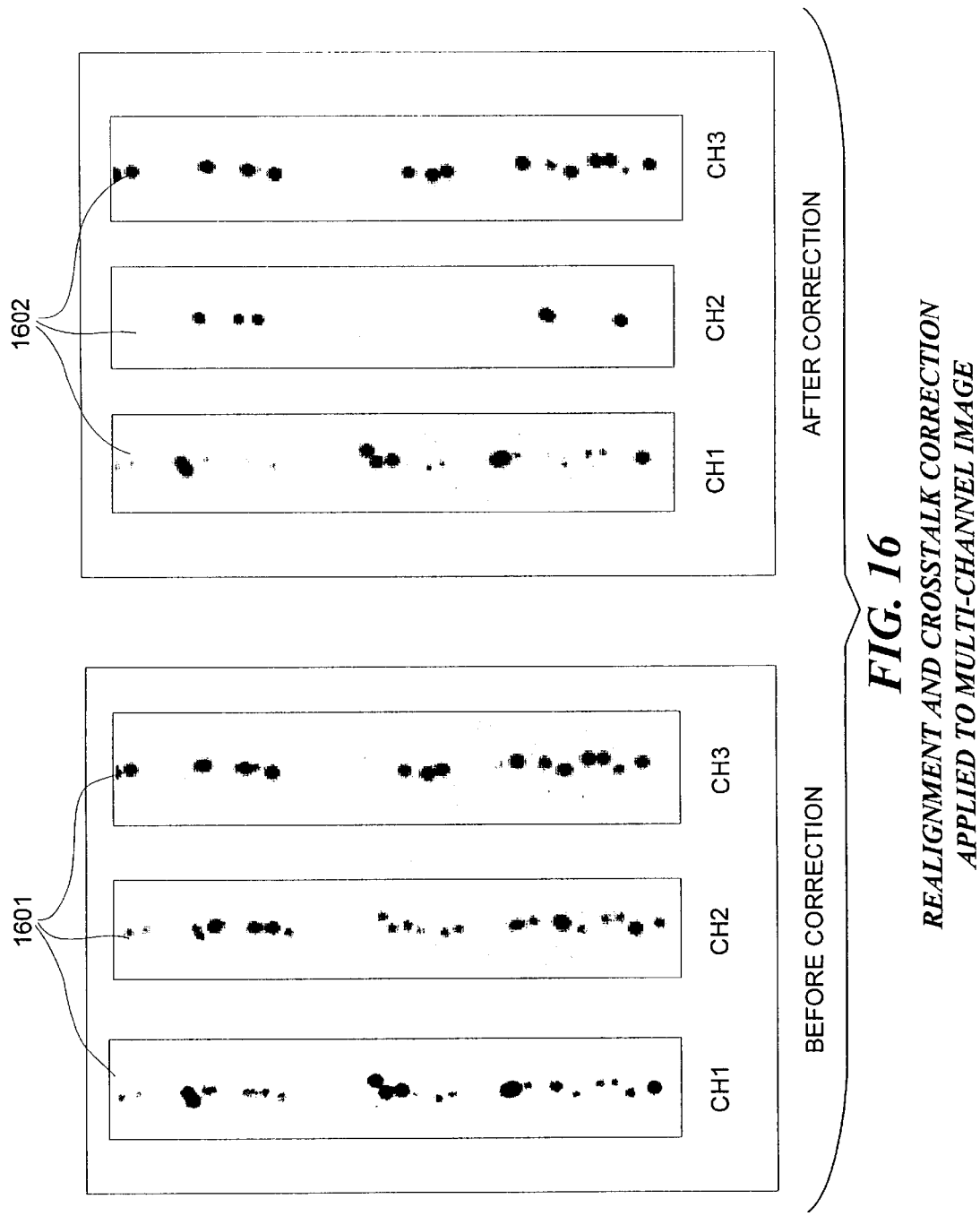
FIG. 16 illustrates grayscale images showing three channels of a multi-parameter flow imaging system, both before and after the application of spatial and spectral corrections made in accord with the present invention.

FIG. 16 illustrates the effectiveness of the method of crosstalk correction 20 of the present invention. Uncorrected images 1601 were synthesized using the following system of equations:

$$I_1(i,j) = \alpha_{11} s_1(i,j) + \alpha_{12} s_2(i,j) + \alpha_{13} s_3(i,j)$$

$$I_2(i,j) = \alpha_{21} s_1(i,j) + \alpha_{22} s_2(i,j) + \alpha_{23} s_3(i,j),$$

and $$I_3(i,j) = \alpha_{31} s_1(i,j) + \alpha_{32} s_2(i,j) + \alpha_{33} s_3(i,j) \quad (30)$$

where $I_m(i,j)$ is an image intensity from channel m at pixel i, j, $s_n(i,j)$ is a signal from source n at pixel i, j, and $\alpha_{mn}$ is a weighting coefficient for source n into channel m.

Each object in the synthesized images is assigned to a particular source and appears in only one channel, in the absence of crosstalk. A comparison of corrected images 1602 with uncorrected images 1601 shows that the correction separates the objects into their respective channels with very little residual error.

Additional Exemplary Preferred Embodiments of Imaging Systems

FIGS. 17–29 and the following descriptions disclose various embodiments of imaging systems and detectors that can be employed to generate multichannel image data, which then can be processed using the method described above to reduce crosstalk among the plurality of channels. It should be noted that none of these embodiments of imaging systems specifically show signal processing means 106 (see FIGS. 1A and 1B). However, it will be understood that signal processing means 106 is readily coupled to the detectors of FIGS. 17–29 to enable the signals generated by such detectors to be processed in accord with the present invention.

Figure 17:
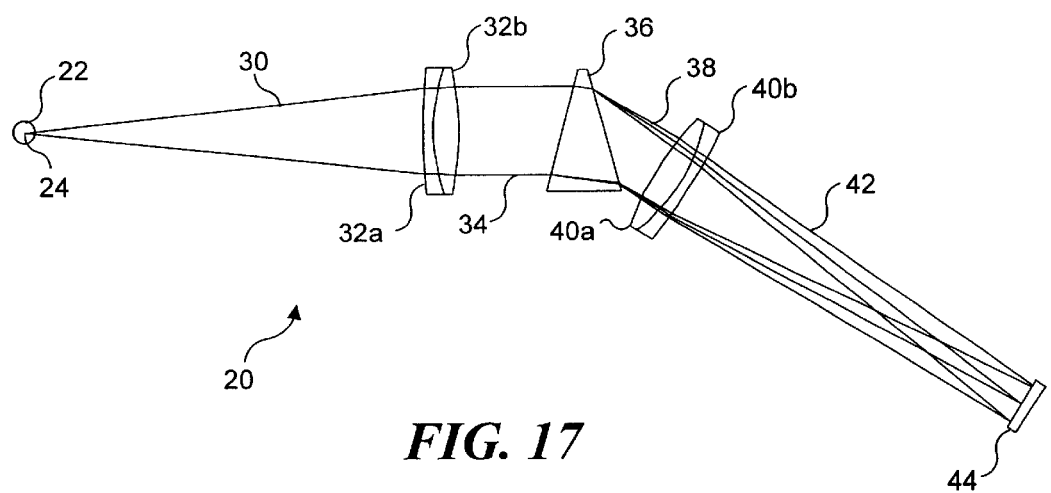
FIG. 17 is a plan view of a first embodiment of the present invention in which particles conveyed by a fluid stream (at left side of Figure) are depicted as flowing into the sheet.
Figure 18:
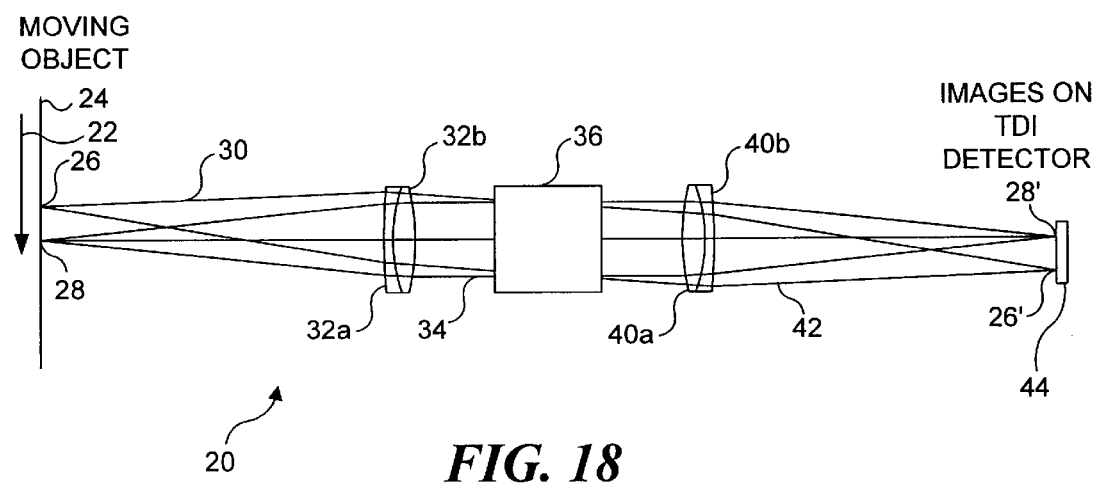
FIG. 18 is a side elevational view of the first embodiment shown in FIG. 17.
Figure 19:
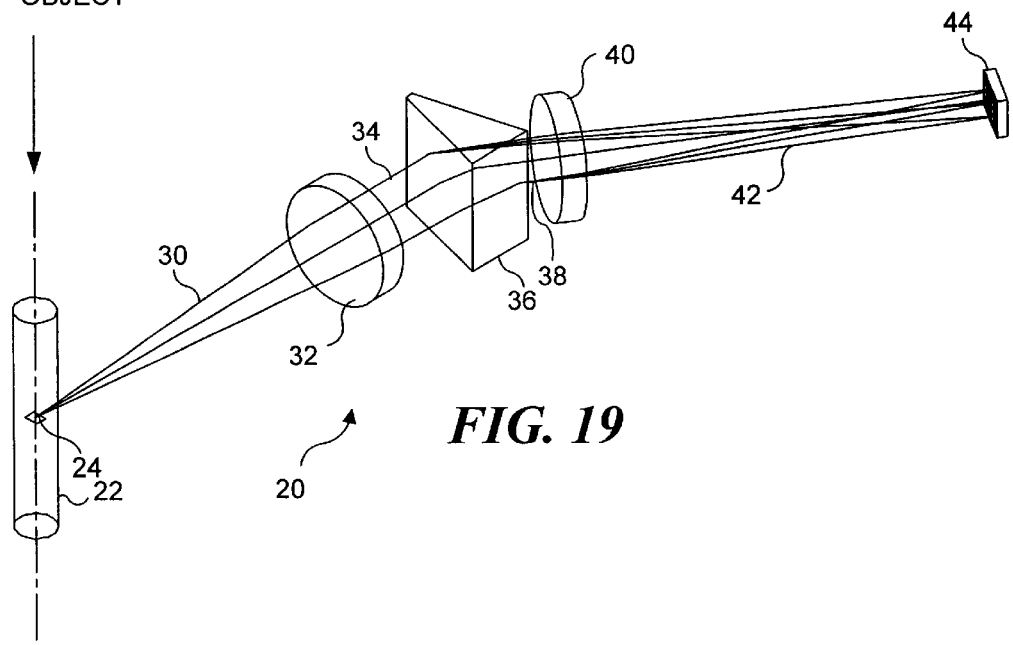
FIG. 19 is an isometric view of the first embodiment of FIG. 17.

A first additional preferred embodiment of an imaging system 20 in accord with the present invention is schematically illustrated in FIGS. 17, 18, and 19, in connection with producing images of moving objects such as cells that are conveyed by a fluid flow 22 through the imaging system. In FIG. 17, fluid flow 22 entrains an object 24 (such as a cell, but alternatively, a small particle) and carries the object through the imaging system. The direction of the fluid flow in FIG. 17 is into (or out of) the sheet, while in FIGS. 18 and 19, the direction of flow is from top to bottom, as indicated by the arrow to the left of the Figures. Light 30 from object 24 passes through collection lenses 32a and 32b that collect the light, producing collected light 34, which is approximately focussed at infinity, i.e. the rays of collected light from collection lens 32b are generally parallel. Collected light 34 enters a prism 36, which disperses the light, producing dispersed light 38. The dispersed light then enters imaging lenses 40a and 40b, which focuses light 42 onto a TDI detector 44.

As will be evident in FIG. 18, if the Figure depicts the imaging of object 24 over time, the object is shown at both a position 26 and a position 28 as it moves with fluid flow 22. As a consequence, images of object 24 will be produced on the detector at two discrete spatial positions 26' and 28', as indicated on the right side of FIG. 18. Alternatively, if FIG. 18 is depicting a single instant in time, positions 26 and 28 can represent the location of two separate objects, which are simultaneously imaged on the detector at positions 26' and 28'.

In regard to imaging system 20 and all other imaging systems illustrated herein, it will be understood that the lenses and other optical elements illustrated are shown only in a relatively simple form. Thus, the collection lens is illustrated as a compound lens comprising only collection lenses 32a and 32b. Lens elements of different designs, either simpler or more complex, could be used in constructing the imaging system to provide the desired optical performance, as will be understood by those of ordinary skill in the art. The actual lenses or optical elements used in the imaging system will depend upon the particular type of imaging application for which the imaging system will be employed.

In each of the embodiments of the present invention, it will be understood that relative movement exists between the object being imaged and the imaging system. In most cases, it will be more convenient to move the object than to move the imaging system. However, it is also contemplated that in some cases, the object may remain stationary and the imaging system move relative to it. As a further alternative, both the imaging system and the object may be in motion but either in different directions or at different rates.

The TDI detector that is used in the various embodiments of the present invention preferably comprises a rectangular charge-coupled device (CCD) that employs a specialized pixel readout algorithm, as explained below. Non-TDI CCD arrays are commonly used for two-dimensional imaging in cameras. In a standard CCD array, photons that are incident on a pixel produce charges that are trapped in the pixel. The photon charges from each pixel are read out of the detector array by shifting the charges from one pixel to the next, and then onto an output capacitor, producing a voltage proportional to the charge. Between pixel readings, the capacitor is discharged and the process is repeated for every pixel on the chip. During the readout, the array must be shielded from any light exposure to prevent charge generation in the pixels that have not yet been read.

In one type of TDI detector 44, which comprises a CCD array, the CCD array remains exposed to the light as the pixels are read out. The readout occurs one row at a time from the top toward the bottom of the array. Once a first row is read out, the remaining rows are shifted by one pixel in the direction of the row that has just been read. If the object being imaged onto the array moves in synchrony with the motion of the pixels, light from the object is integrated for the duration of the TDI detector's total readout period without image blurring. The signal strength produced by a TDI detector will increase linearly with the integration period, which is proportional to the number of TDI rows, but the noise will increase only as the square root of the integration period, resulting in an overall increase in the signal-to-noise ratio by the square root of the number of rows. One TDI detector suitable for use in the present invention is a Dalsa Corp., Type IL-E2 image sensor, although other equivalent or better image sensors can alternatively be used. The Dalsa image sensor has 96 stages or rows, each comprising 512 pixels; other types of image sensors useable in the present invention may have different configurations of rows and columns or a non-rectilinear arrangement of pixels. The Dalsa sensor has approximately 96 times the sensitivity and nearly 10 times the signal-to-noise ratio of a standard CCD array. The extended integration time associated with TDI detection also serves to average out temporal and spatial illumination variations, increasing measurement consistency.

In imaging system 20 and in other embodiments of the present invention that employ a fluid flow to carry objects through the imaging system, a flow-through cuvette or a jet (not shown) contains the cells or other objects being analyzed. The velocity and cellular concentration of the fluid may be controlled using syringe pumps, gas pressure, or other pumping methods (not shown) to drive a sample solution through the system to match the pixel readout rate of the TDI detector. However, it should be understood that the readout rate of the TDI detector could be selectively controlled, as required, to match the motion of the sample solution.

Various optical magnifications can be used to achieve a desired resolution of the object that is being imaged on the light sensitive regions (pixels) of the TDI detector. It is contemplated that in most embodiments, the optical magnification will fall within a range of 1:1 to 50:1, providing a substantial range in the number of light sensitive regions on the TDI detector on which images of the object are formed, also depending of course, on the actual size of the object being imaged and its distance from the imaging system. It is envisioned that the present invention can have applications ranging from the analysis of cells and other microscopic objects to the imaging of stellar objects.

It should be emphasized that the present invention is not limited to CCD types of TDI detectors. Other types of TDI detectors, such as complementary metal oxide semiconductor (CMOS) and multichannel plate imaging devices might also be used for the TDI detector in the present invention. It is important to understand that any pixilated device (i.e., having a multitude of light sensitive regions) in which a signal produced in response to radiation directed at the device can be caused to move through the device in a controlled fashion is suitable for use as the TDI detector in the present invention. Typically, the signal will move in synchrony with a moving image projected onto the device, thereby increasing the integration time for the image, without causing blurring. However, the motion of the signal can be selectively desynchronized from the motion of the radiation image, as required to achieve a desired affect.

Figure 20:
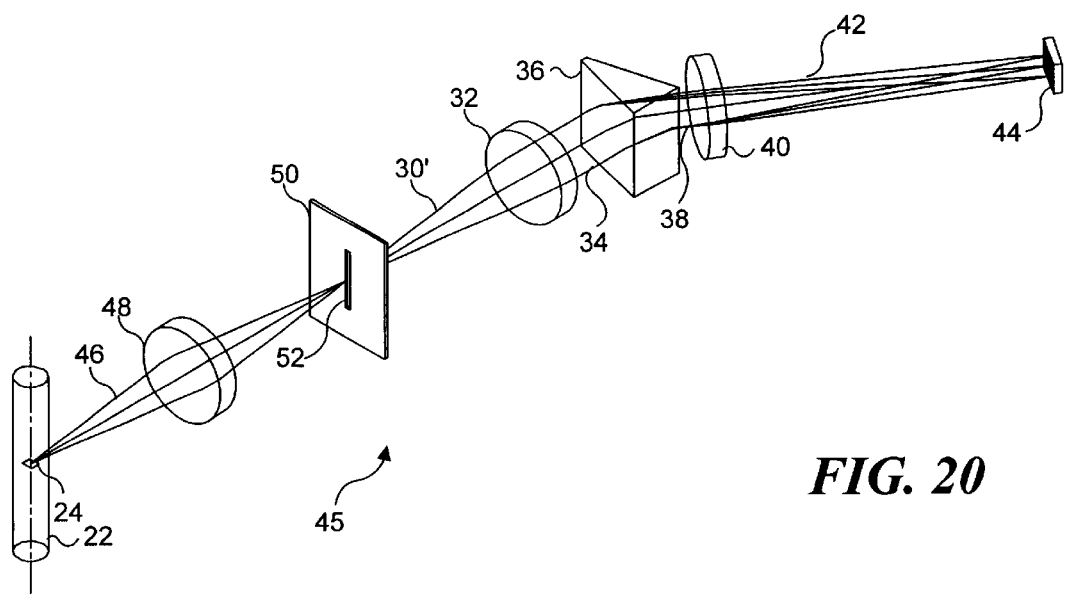
FIG. 20 is an isometric view of a confocal embodiment that includes a slit for spatial filtering of extraneous light.

FIG. 20 illustrates an imaging system 45, which is similar in many ways to imaging system 20. However, imaging system 45 is a confocal embodiment that includes a plate 50 having a slit 52 that substantially prevents extraneous light from reaching TDI detector 44. In imaging system 45, light 46 from object 24 is focussed by an objective lens 48 onto a slit 52. Slit 52, as shown in FIG. 20, is sufficiently narrow to block light that is not focussed onto the slit by objective lens 48 from passing through the slit. Light 30' passes through the slit and is collected by collection lens 32 as discussed above, in regard to imaging system 20. Collected light 34 is spectrally dispersed by prism 36, and is imaged by imaging lens 40 onto TDI detector 44, also as discussed above. By excluding light other than that from object 24 from reaching TDI detector 44, the TDI detector produces an output signal that corresponds only to the actual images of the object, and the signal is not affected by the extraneous light, which has been excluded. If not excluded in this manner, the ambient light reaching TDI detector 44 might otherwise produce "noise" in the output signal from the TDI detector.

It should be noted that in the illustration of each of imaging systems 20 and 45, a light source has not been shown. These first two embodiments have been illustrated in their most general form to make clear that a separate light source is not required to produce an image of the object, if the object is luminescent, i.e., if the object produces light. However, many of the applications of the present invention will require that one or more light sources be used to provide light that is incident on the object being imaged. The location of the light sources substantially affects the interaction of the incident light with the object and the kind of information that can be obtained from the images on the TDI detector.

Figure 21:
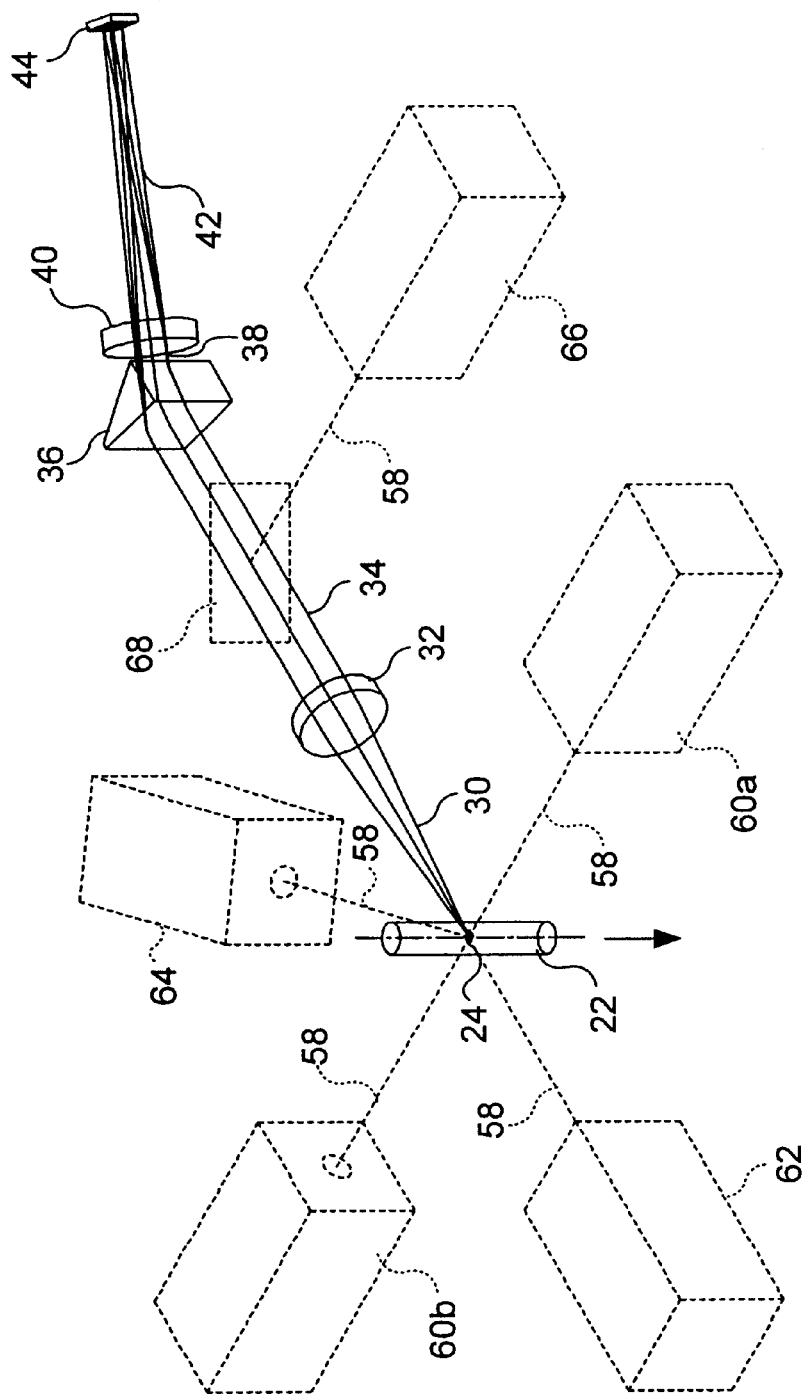
FIG. 21 is an isometric view showing different locations for a light source in connection with the first embodiment.

In FIG. 21, several different locations of light sources usable to provide light incident on object 24 are illustrated. It should be understood, however, that light sources could be located at many other positions besides those shown in FIG. 21. The location of each one or more light source employed will be dependent upon the kind of imaging of the object, and the kind of data for the object, to be derived from the signal produced by the TDI detector. For example, employing a light source 60a or a light source 60b, as shown in the Figure, will provide light 58 that is incident on object 24 and which is scattered from the object into the optical axis of collection lens 32. The optical axis of collection lens 32 is at about a 90° angle relative to the directions of the light incident upon object 24 from either light source 60a or 60b.

In contrast, a light source 62 is disposed so that light 58 emitted from the source travels toward the object in a direction that is generally aligned with the optical axis of collection lens 32, so that the image formed on TDI detector 44 will not include light absorbed by object 24. Light absorption characteristics of the object can thus be determined by illuminating the object using a light source 62.

A light source 64 is disposed to illuminate object 24 with light directed toward the object along a path that is approximately 30–45° off the optical axis of collection lens 32. This light 58, when incident on object 24 will be reflected (scattered) from object 24, and the reflected or scattered light will be imaged on TDI detector 44. A more directly reflected light is provided by an epi light source 66, disposed so as to direct its light 58 toward a partially reflective surface 68 that is disposed so that a portion of the light is reflected through collection lens 32 and onto object 24. The light reaching the object will be reflected from it back along the axis of collection lens 32 and will at least in part pass through partially reflective surface 68 to form an image of the object on TDI detector 44. Alternatively, a dichroic mirror may be employed instead of, and in the position of, partially reflective surface 68 to direct light from epi light source 66 to excite fluorescence or other stimulated emission from object 24. Emission from object 24 is then at least partially collected by collection lens 32 and passes through the dichroic mirror for spectral dispersion and detection by the TDI detector.

In addition to imaging an object with the light that is incident on it, a light source can also be used to stimulate emission of light from the object. For example, FISH probes that have been inserted into cells will fluoresce when excited by light, producing a corresponding characteristic emission spectra from any excited FISH probe that can be imaged on TDI detector 44. In FIG. 21, light sources 60a, 60b, 64, or 66 could alternatively be used for causing the excitation of FISH probes on object 24, enabling TDI detector 44 to image FISH spots produced by the FISH probes on the TDI detector at different locations as a result of the spectral dispersion of the light from the object that is provided by prism 36. The disposition of these FISH spots on the TDI detector surface will depend upon their emission spectra and their location in the object. Use of FISH probes in connection with producing images of FISH spots on the TDI detector with the present invention is discussed in greater detail below.

Each of the light sources illustrated in FIG. 21 produces light 58, which can either be coherent, non-coherent, broadband or narrowband light, depending upon the application of the imaging system desired. Thus, a tungsten filament light source can be used for applications in which a narrowband light source is not required. For applications such as stimulating the emission of fluorescence from FISH probes, narrowband laser light is preferred, since it also enables a spectrally-decomposed, non-distorted image of the object to be produced from light scattered by the object. This scattered light image will be separately resolved from the FISH spots produced on TDI detector 44, so long as the emission spectra of any FISH spots are at different wavelengths than the wavelength of the laser light. The light source can be either of the continuous wave (CW) or pulsed type. If a pulsed type illumination source is employed, the extended integration period associated with TDI detection can allow the integration of signal from multiple pulses. Furthermore, it is not necessary for the light to be pulsed in synchronization with the TDI detector.

Pulsed lasers offer several advantages over CW lasers as a light source in the present invention, including smaller size, higher efficiency, higher reliability, and the ability to deliver numerous wavelengths simultaneously. Another advantage of pulsed lasers is their ability to achieve saturating levels of fluorescence excitation of fluorescent probes used in cells. Fluorescence saturation occurs when the number of photons encountering a fluorescent molecule exceeds its absorption capacity. Saturating excitation produced by a pulsed laser is inherently less noisy than unsaturating CW laser excitation because variations in pulse-to-pulse excitation intensity have little effect on the fluorescence emission intensity.

Prism 36 in the imaging systems discussed above can be replaced with a diffraction grating, since either is capable of spectrally dispersing the optical signals from the cells over the pixels of the TDI detector. In addition to providing useful data from a cell or other object, spectral dispersion can be used to reduce measurement noise. In cases where the light source wavelength differs from the emission spectra of the fluorescent probes, the light from the source that is scattered into the collection system is spatially isolated from the fluorescence signals. If the light source wavelength overlaps the emission spectra of the fluorescent probes, the pixels of the TDI detector in which light of the wavelength of the source falls can be isolated from those pixels on which the remaining fluorescence signals fall. Further, by dispersing the fluorescence signals over multiple pixels, the overall dynamic range of the imaging system is increased.

Third Additional Exemplary Preferred Embodiment

Figure 22:
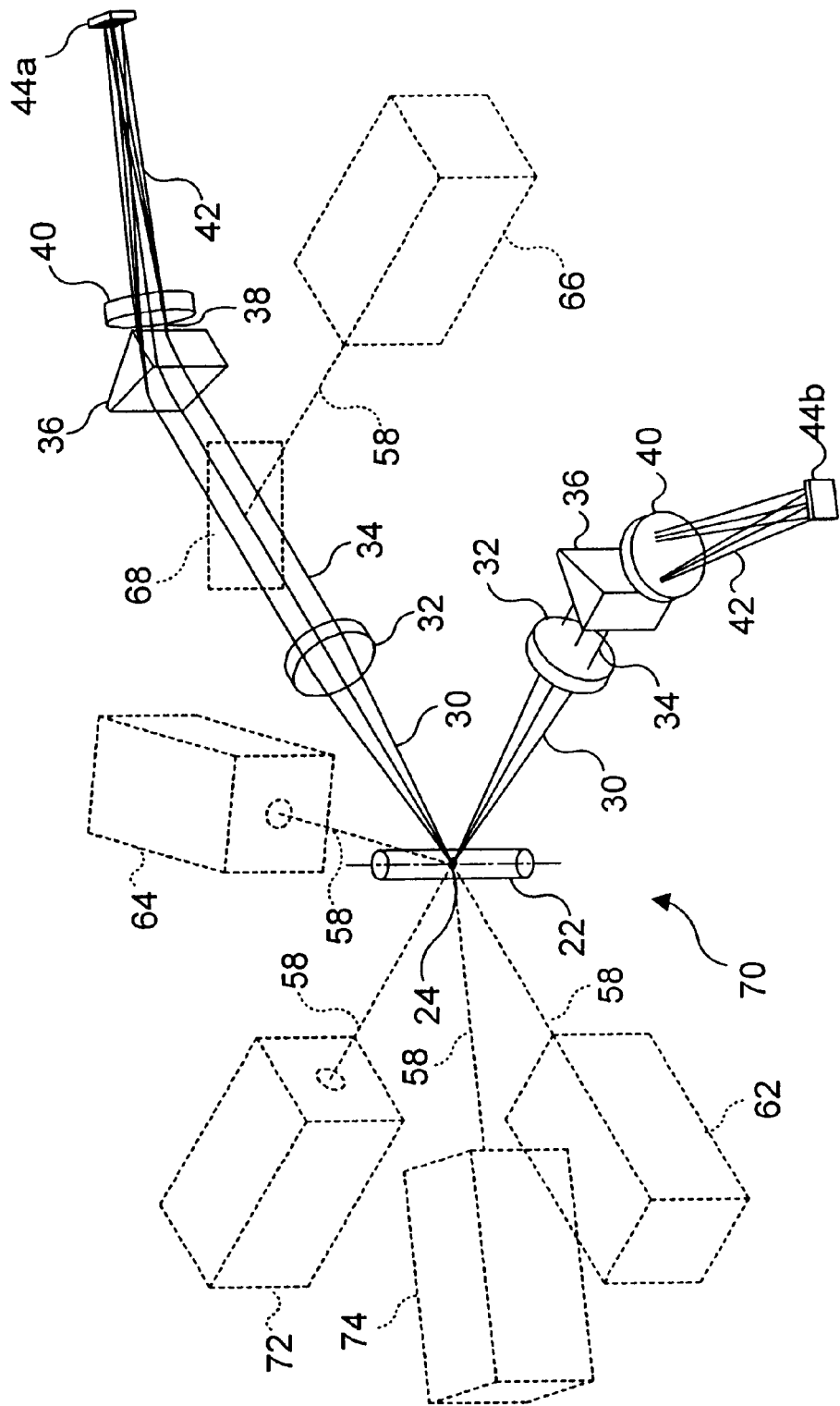
FIG. 22 is an alternative to the first embodiment in which a second set of imaging components and a second TDI detector is included for monitoring light from a particle, to avoid interference between Fluorescent In Situ Hybridization (FISH) probes, and showing alternative locations for light sources.

A third additional preferred embodiment of an imaging system with which the present invention is useful is directed to a stereoscopic arrangement, as illustrated in FIG. 22. This arrangement enables the imaging of the object from two different directions in order to distinguish features that would otherwise overlap when viewed from a single direction. While the third preferred embodiment can be employed for objects on moving substrates such as microscope slides, it is particularly useful for analyzing multicomponent objects in solution, such as cells containing FISH probes. Such probes appear as point sources of light anywhere within the cell's three-dimensional nucleus. In some cases, two or more FISH probes may appear in an overlapping relationship along the optical axis of the imaging system. In such cases, one of the FISH probes may obscure the others, making it difficult to determine the number of probes present in the cell. This problem of overlapping is a key factor in the determination of genetic abnormalities such as trisomy, otherwise known as Down's syndrome. Single-perspective systems may address this problem by "panning through" the object along the optical axis to acquire multiple image planes in the object. While this approach may be effective, it requires a significant amount of time to collect multiple images and cannot be readily applied to a cell in flow. The stereoscopic imaging system 70 in FIG. 22 includes two TDI detectors 44a and 44b, and their associated optical components, as discussed above in connection with imaging system 20.

By positioning the optical axes of collection lenses 32 for the two TDI detectors so that they are spaced apart, for example, by 90°, it is possible to separately resolve the FISH spots imaged from two or more FISH probes on at least one of TDI detectors 44a or 44b. If two or more FISH probes overlap in regard to the image produced on one of the detectors, they will be separately resolved in the spectrally dispersed images produced on the other TDI detector. Further, the use of two TDI detectors in imaging system 70 in what might be referred to as a "stereo or three-dimensional configuration" allows flexibility in the configuration of each leg of the system, including parameters such as the relative TDI readout rates, axial orientations, inclinations, focal plane positions and magnification. Multiple cells or other objects may be imaged onto each detector simultaneously in the vertical direction. Since the objects may move in synchronicity with the signal on the TDI, no gate or shutter is required to prevent blurring of the image. As previously noted, the present invention can use a pulsed or CW light source without need for a trigger mechanism to time a pulse coincident with particle arrival in the field of view. If a pulsed light source is used, the extended field of view in the axis of motion associated with TDI detection allows the cell or object in motion to be illuminated by multiple pulses during its traversal. In contrast to a frame-based imaging apparatus, a TDI system can produce a single unblurred image of the object that integrates the signal from multiple pulses. When a CW light source is used, the signal generated by the object will be collected throughout the entire traversal of the object through the field of view, as opposed to only a small segment in time when a shutter is open. Therefore, the amount of signal collected and imaged on the detector in the present invention is substantially greater than that of the prior art frame-based imaging systems. Consequently, the present invention can operate at very high throughput rates with excellent signal to noise ratio.

Also illustrated in FIG. 22 are several exemplary positions for light sources, which are useful for different purposes in connection with the imaging system illustrated therein. In connection with TDI detector 44a, light source 62 provides illumination of object 24 from a direction so that absorption characteristics of the object can be determined from the image produced on the TDI detector. At the same time, light provided by light source 62 that is scattered from object 24 can be used to produce a scatter image and spectrally dispersed images on TDI detector 44b. Light source 74 can be employed to produce spectrally dispersed and scattered images on both TDI detectors 44a and 44b. If light sources 62 and 72 are of different wavelengths and an appropriate filter is provided to block the wavelength from the light source aligned with the optical axis of the respective collections lenses 32, these two light sources can be used for producing scattered light from the object. For example, suppose light source 72 produces light of a wavelength A that scatters from object 24 and is directed toward TDI detector 44a. By including a filter (not shown) that blocks wavelength B produced by light source 62, the light at wavelength B will not directly affect the images produced on TDI detector 44a. Similarly, the light from light source 72 would be blocked with an appropriate filter (not shown) so that it does not interfere with the imaging of light produced by light source 62 that is scattered from object 24 onto TDI detector 44b.

Epi light source 66 is also illustrated for use in producing images on TDI detector 44a in conjunction with partial reflector 68. Light source 64 can be used to generate reflected light to produce images on TDI detector 44a, while scattered light from this source is directed toward TDI detector 44b. These and other possible locations of light sources will be apparent to those of ordinary skill in the art, as appropriate for providing the incident light on the object needed to achieve imaging, depending upon the particular application and information about the object that is desired.

Imaging Slide or Object Carried by Slide

Figure 23:
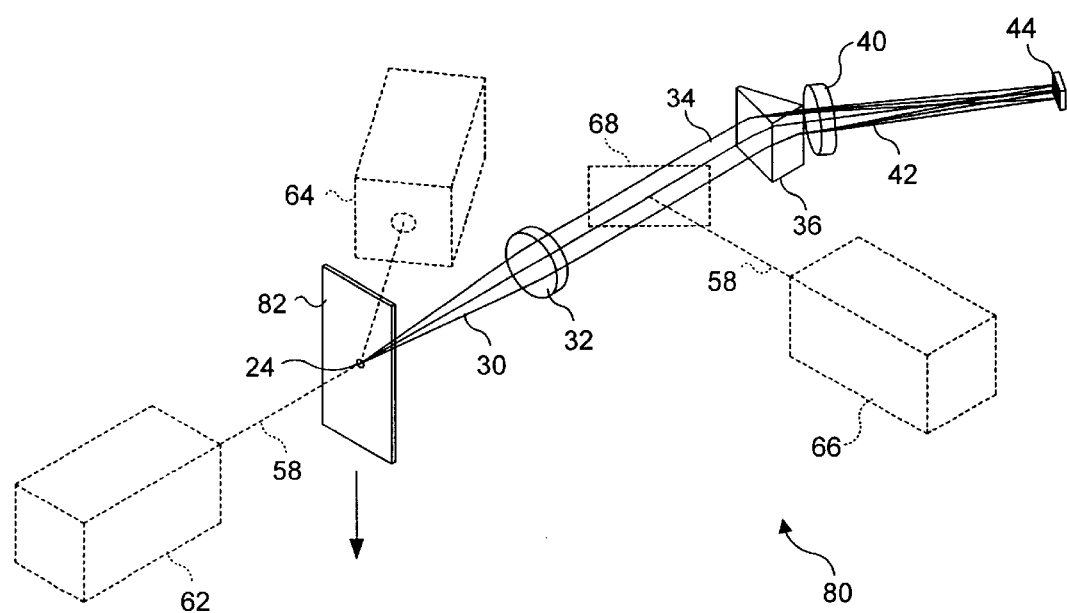
FIG. 23 is an isometric view of an embodiment in which an object is supported by a slide or substrate that moves past a collection lens, showing different locations for a light source.

Turning now to FIG. 23, an imaging system 80 is illustrated that is similar to imaging system 20, except that it is used for imaging object 24 on a slide 82 (or other moving substrate). Object 24 is supported by slide 82 and the slide moves relative to the imaging system as shown in FIG. 23. Alternatively, slide 82 may be the object that is imaged. For example, the object may be a semiconductor wafer, paper, or other object of interest, since the object may be imaged using reflected incident light.

To provide light incident on either slide 82 or object 24 that is supported thereby, a light source can be placed at one of several different locations. Exemplary light sources 62, 64, and 66 illustrate some of the locations at which light sources useful in this embodiment may be disposed. Light 58 emitted by any of the light sources can be either coherent or non-coherent light, pulsed or CW, and can be directed through slide 82 (if it is transparent) from light source 62 or can be reflected from the object or slide, if light sources 64 or 66 are employed. As noted previously, epi light source 66 illuminates the object in connection with a partially reflective surface 68.

Figure 24A:
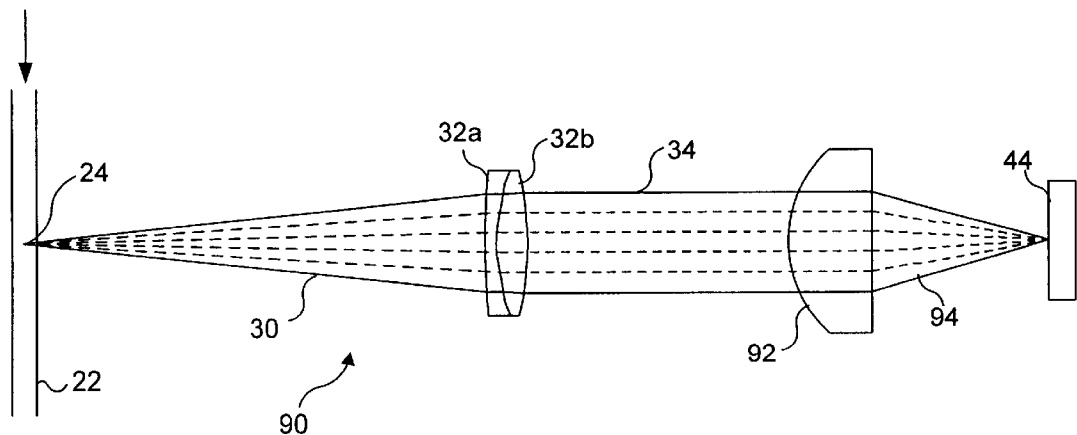
FIGS. 24A and 24B are respectively a plan view and a side elevational view of an alternative to the embodiment of FIG. 23, which is used to produce a scattered pattern on the TDI detector.
Figure 24B:
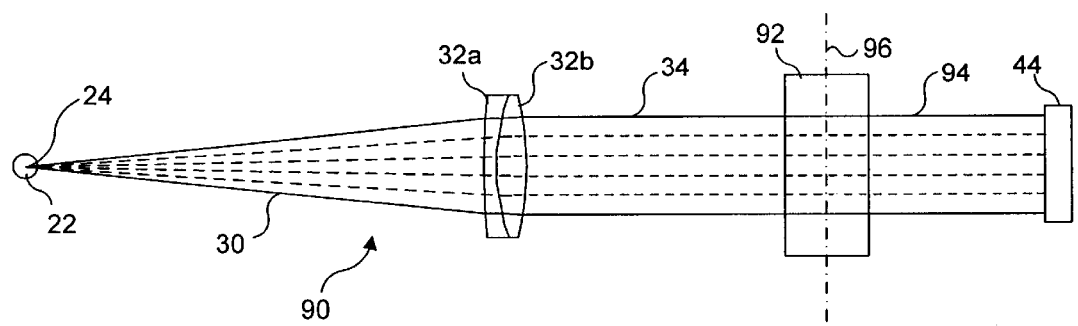

FIGS. 24A and 24B show two different views of yet another preferred embodiment, which is an imaging system 90 that produces a scattered pattern image of object 24 on TDI detector 44. Light 30 from object 24 passes through collection lenses 32a and 32b, and collected light 34 is directed onto a cylindrical lens 92, as in the previous embodiments. Cylindrical lens 92 focuses light 94 on TDI detector 44, generally along a line that is aligned with a central axis 96 of cylindrical lens 92. Central axis 96 is shown in FIG. 24B, and it will be apparent that it is orthogonal to the direction in which object 24 moves through the imaging system. As object 24 moves downwardly, relative to its disposition as shown in FIG. 24A, the focus of cylindrical lens 92 on TDI detector 44 moves upwardly. Cylindrical lens 92 thus distributes an image of the object along a row or rows of the light sensitive regions or pixels of TDI detector 44.

Figure 25:
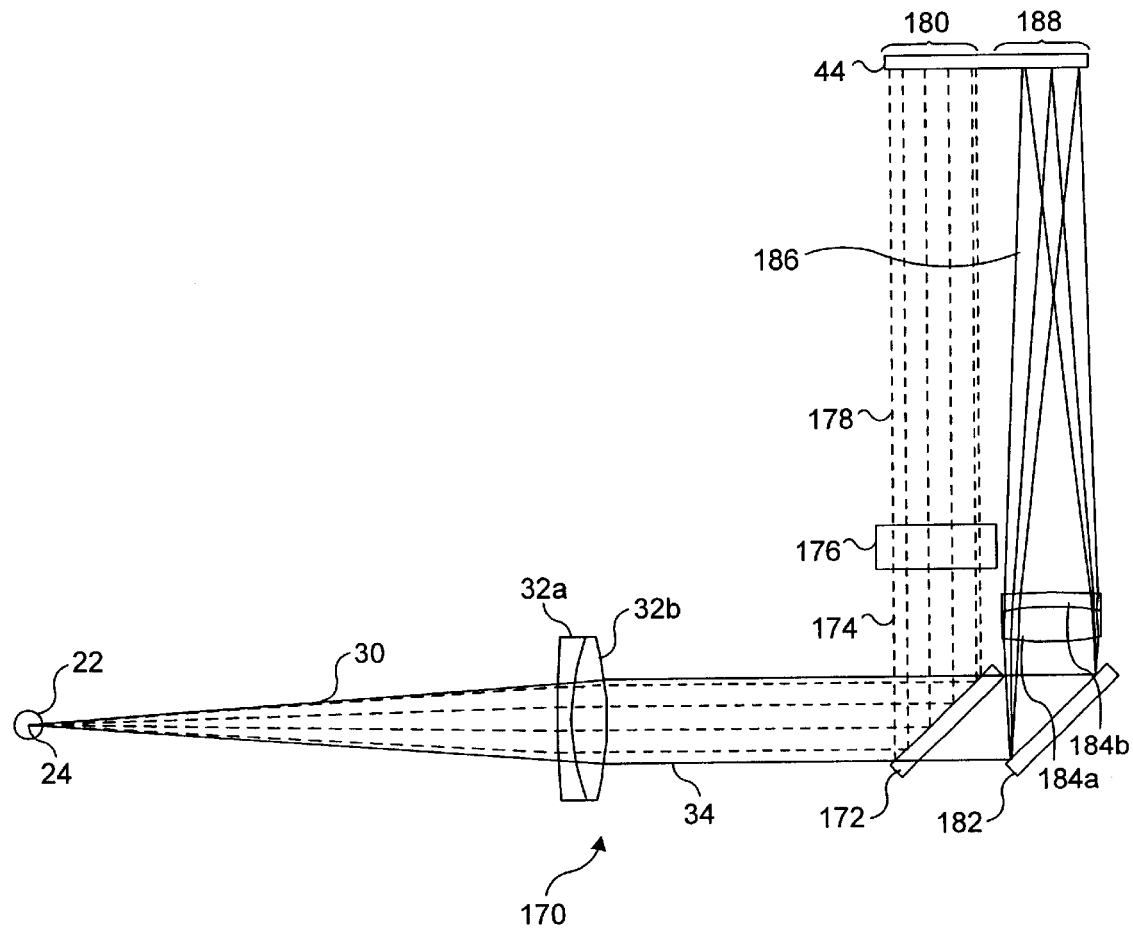
FIG. 25 is a plan view of yet a further embodiment in which light forming a scatter patterned image and spectrally dispersed light from an object are imaged on separate portions of a TDI detector.

Referring now to FIG. 25, an illustration is provided of an imaging system 170 that produces both a scattered pattern image and a spectrally dispersed image of object 24 on TDI detector 44. In imaging system 170, light 30 from object 24 passes through collections lenses 32a and 32b, which produce infinitely focussed light 34 directed toward a dichroic filter 172. Dichroic filter 172 reflects light of a specific wavelength, e.g., the wavelength of a light source (not shown) that is incident upon object 24. Light of any other wavelength is transmitted through dichroic filter 172 toward a diffraction grating 182. Diffraction grating 182 spectrally disperses the light transmitted through dichroic filter 172, which typically would be light produced by the fluorescence of FISH probes on object 24, so that a plurality of FISH spots corresponding to the number of different FISH probes and objects being imaged are produced on TDI detector 44.

Light 174, which is reflected from dichroic filter 172, is transmitted into cylindrical lens 176 yielding focused light 178 directed along a line as a scattered pattern image in a region 180 on the TDI detector. The spectrally dispersed images of FISH spots or other aspects of object 24 having wavelengths different than that reflected by dichroic filter 172 are imaged as light 186 by imaging lenses 184a and 184b onto a region 188 of the TDI detector. Thus, signals corresponding to the scattered pattern image and the spectrally dispersed images are both produced by TDI detector 44.

Figure 26:
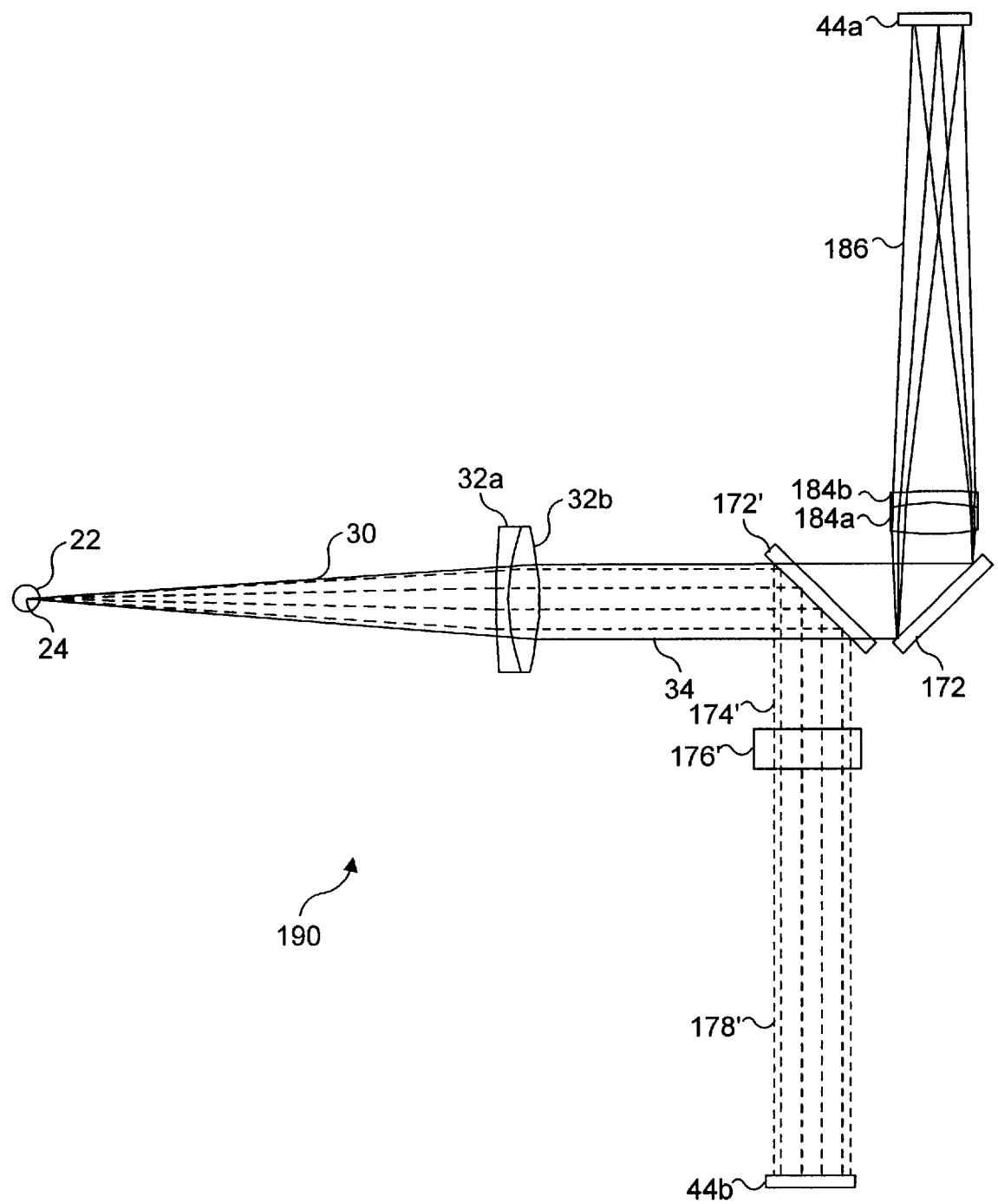
FIG. 26 is a plan view of a still further embodiment in which light forming a scatter patterned image and spectrally dispersed light from the object are imaged on two different TDI detectors.

In FIG. 26, an imaging system 190 is illustrated that is slightly different than the preceding embodiment, since a dichroic filter 172' is employed that is angled in a different direction, toward a second TDI detector 44b. A dispersed pattern image represented by light 178' is produced by a cylindrical lens 176' in this embodiment. Just as in imaging system 170, light transmitted through dichroic filter 172' is focused onto TDI detector 44a. Aside from using two separate TDI detectors that are disposed at different sides of the imaging system, imaging system 190 is substantially identical in operation to imaging system 170. However, just as in the third preferred embodiment, the use of two separate TDI detectors allows flexibility in the configuration of each leg of the system, including parameters such as the relative TDI readout rates, axial orientations, inclinations, focal plane positions, and magnification. It should also be noted that imaging system 170 could be constructed to include two separate TDI detectors instead of a single TDI detector, if desired.

Non-Distorting Spectral Dispersion Systems

The present invention can be provided with a spectral dispersion filter assembly that does not convolve the image with the emission spectra of the light forming the image, thereby eliminating the need for deconvolution of the emission spectra from the image. FIG. 27 illustrates an embodiment of such a non-distorting spectral dispersion system 250 that employs a five color stacked wedge spectral dispersing filter assembly 252. This embodiment is substantially similar to the embodiment shown in FIGS. 17, 18, and 19, except that spectral dispersing prism element 36 (of FIGS. 17, 18, and 19) is replaced by spectral dispersing filter assembly 252. The spectral dispersing filter assembly splits the light into a plurality of light beams having different bandwidths. Each light beam thus produced is directed at a different nominal angle so as to fall upon a different region of TDI detector 44. The nominal angular separation between each bandwidth produced by the spectral dispersing filter assembly 252 exceeds the field angle of the imaging system in object space thereby preventing overlap of the field images of various bandwidths on the detector.

Spectral dispersing filter assembly 252 comprises a plurality of stacked dichroic wedge filters, including a red dichroic filter R, an orange dichroic filter O, a yellow dichroic filter Y, a green dichroic filter G, and a blue dichroic filter B. Red dichroic filter R is placed in the path of collected light 34, oriented at an angle of approximately 44.0° relative to an optic axis 253 of collection lenses 32a and 32b. Light of red wavelengths and above, i.e., >640 nm, is reflected from the surface of red dichroic filter R at a nominal angle of 1°, measured counter-clockwise from a vertical optic axis 257. The light reflected by red dichroic filter R leaves spectral dispersing filter assembly 252 and passes through imaging lenses 40a and 40b, which cause the light to be imaged onto a red light receiving region of TDI detector 44, which is disposed toward the right end of the TDI detector, as shown in FIG. 27.

Orange dichroic filter O is disposed a short distance behind red dichroic filter R and is oriented at an angle of 44.5 degrees with respect to optic axis 253. Light of orange wavelengths and greater, i.e., >610 nm, is reflected by orange dichroic filter O at a nominal angle of 0.5° with respect to vertical optic axis 257. Because the portion of collected light 34 comprising wavelengths longer than 640 nm was already reflected by red dichroic filter R, the light reflected from the surface of orange dichroic filter O is effectively bandpassed in the orange colored region between 610 nm and 640 nm. This light travels at a nominal angle of 0.5° from vertical optic axis 257, and is imaged by imaging lenses 40a and 40b so as to fall onto an orange light receiving region disposed toward the right hand side of TDI detector 44 between a center region of the TDI detector and the red light receiving region, again as shown in FIG. 27.

Yellow dichroic filter Y is disposed a short distance behind orange dichroic filter O and is oriented at an angle of 45° with respect to optic axis 253. Light of yellow wavelengths, i.e., 560 nm and longer, is reflected from yellow dichroic filter Y at a nominal angle of 0.0° with respect to vertical optic axis 257. Wavelengths of light reflected by yellow dichroic filter Y are effectively bandpassed in the yellow region between 560 nm and 610 nm and are imaged by imaging lenses 40a and 40b near vertical optic axis 257 so as to fall on a yellow light receiving region toward the center of TDI detector 44.

In a manner similar to dichroic filters R, O, and Y, dichroic filters G and B are configured and oriented so as to image green and blue light wavebands onto respective green and blue light receiving regions of TDI detector 44, which are disposed toward the left-hand side of the TDI detector. By stacking the dichroic filters at different predefined angles, spectral dispersing filter assembly 252 collectively works to focus light within predefined wavebands of the light spectrum onto predefined regions of TDI detector 44. Those of ordinary skill in the art will appreciate that the filters used in the spectral dispersing filter assembly 252 may have spectral characteristics that differ from those described above. Further, the spectral characteristics may be arbitrary and not limited to dichroic in order to achieve the desired dispersion characteristics.

The wedge shape of the dichroic filters in the preceding discussion allows the filters to be placed in near contact, in contact or possibly cemented together to form the spectral dispersing filter assembly 252. The angle of the wedge shape fabricated into the substrate for the dichroic filter allows easy assembly of the spectral dispersing filter assembly 252, forming a monolithic structure in which the wedge-shaped substrate is sandwiched between adjacent dichroic filters. If the filters are in contact with each other or cemented together, the composition of the materials that determine the spectral performance of the filter may be different from those which are not in contact. Those of ordinary skill in the art will appreciate that flat, non wedge-shaped substrates could be used to fabricate the spectral dispersing filter assembly 252. In this case another means such as mechanically mounting the filters could be used to maintain the angular relationships between the filters.

In addition to the foregoing configuration, non-distorting spectral dispersion system 250 may optionally include a detector filter assembly 254 to further attenuate undesired signals in each of the light beams, depending upon the amount of rejection required for out-of-band signals. FIG. 29 illustrates the construction of an exemplary detector filter 254 corresponding to the five color bands discussed above and includes a blue spectral region 256, a green spectral region 258, a yellow spectral region 260, an orange spectral region 262, and a red spectral region 264, all of which are disposed side-by-side, as shown in the Figure. The detection filter assembly shown in FIG. 29 may be constructed by mounting separate filters in side-by-side arrangement on a common substrate. Additionally, the ordinary practitioner in the art will understand that the filter may alternatively be placed at an intermediate image plane, instead of directly in front of TDI detector 44.

In the embodiment shown in FIG. 27, light may pass through each dichroic filter in the spectral dispersing filter assembly 252 twice before exiting the spectral dispersing filter assembly 252. This condition will further attenuate out-of-band signals, but will also attenuate in-band signals. FIG. 29 illustrates an eighth embodiment of the present invention in which the light does not pass through another dichroic filter after reflection. In this embodiment, a plurality of cube dichroic filters, including a red cube filter 266, a yellow cube filter 268, a green cube filter 270, and a blue cube filter 272 are spaced apart sufficiently to ensure that light does not pass through any of the cube filters more than once. As with the embodiment of FIG. 27, the cube dichroic filters are oriented at appropriate angles to image light within a predefined bandwidth to distinct regions on a TDI detector 274. As the light is reflected from each of cube dichroic filters 266, 268, 270 and 272, it is directed toward imaging lenses 40a and 40b, and different bandpass portions of the light are focussed upon corresponding red, yellow, green, and blue light receiving segments or regions defined on a light receiving surface of TDI detector 274. If desired, an optional detector filter assembly 276 of similar construction to detector filter assembly 254 (but without the orange spectral region) may be used to increase the rejection of out-of-band signals. It should be apparent to those skilled in the art that separate spaced apart plate, or pellical beam splitters could also be used in this application instead of the cube filters. In the eight embodiment illustrated in FIG. 29, the image lenses 40a and 40b must be placed a sufficient distance away from the plurality of cube filters to minimize the clear aperture requirement for lenses 40a and 40b. Those skilled in the art will appreciate the clear aperture in the plane orthogonal to the page can increase as the distance between the lenses and plurality cube filters increases. Therefore, the placement of lenses 40a and 40b must be chosen to appropriately accommodate the clear aperture in both planes.

The foregoing descriptions of the last two additional preferred embodiments of imaging systems illustrate the use of four and five color systems. Those skilled in the art will appreciate that a spectral dispersing component with more or fewer filters may be used in these configurations in order to construct a system covering a wider or a narrower spectral region, or different passbands within a given spectral region. Likewise, those skilled in the art will appreciate that the spectral resolution of the present invention may be increased or decreased by appropriately choosing the number and spectral characteristics of the dichroic and or bandpass filters that are used. Furthermore, those skilled in the art will appreciate that the angles or orientation of the filters may be adjusted to direct light of a given bandwidth onto any desired point on the TDI detector. In addition, there is no need to focus the light in increasing or decreasing order by wavelength. For example, in fluorescence imaging applications, one may wish to create more spatial separation on the TDI detector between the excitation and emission wavelengths by changing the angles at which the filters corresponding to those wavelengths are oriented with respect to the optic axes of the system. Finally, it will be clear to those skilled in the art that dispersion of the collected light may be performed on the basis of non-spectral characteristics, including angle, position, polarization, phase, or other optical properties.

As with the earlier embodiments discussed above, these embodiments that use the filters will require that one or more light sources be used to provide light that is incident on the object being imaged. Accordingly, various light sources disposed at different positions, such as those shown in FIGS. 21–23 and discussed above, may be used to enhance the image quality produced by each of these embodiments. For clarity and to simplify the explanation of these embodiments, the light sources have been omitted in FIGS. 27 and 29; however, it will be recognized by those skilled in the art how such light sources may be employed in these embodiments, based on the previous discussion of the use of the light sources with respect to the earlier embodiments.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for processing signals from different channels in a multi-channel digital imaging system, said signals comprising image signal data, comprising steps of:
   (a) determining spatial alignment offsets for the image signal data;
   (b) aligning the image signal data by applying the spatial alignment offsets to the image signal data, to produce aligned image signal data;
   (c) determining spectral crosstalk reduction coefficients; and
   (d) applying the spectral crosstalk coefficients to the aligned image signal data, for spectral correction thereof.

2. The method of claim 1, wherein the step of determining spatial alignment offsets comprises the step of determining spatial alignment offsets to within sub-pixel resolution, and wherein the step of aligning the image signal data comprises the step of aligning the image signal data by applying the sub-pixel spatial alignment offsets to the image signal data.

3. The method of claim 1, wherein the step of determining spatial alignment offsets is performed before sample data are captured by the multi-channel digital imaging system.

4. The method of claim 1, wherein the step of determining spatial alignment offsets is performed concurrently with the step of capturing sample data with the multi-channel digital imaging system.

5. The method of claim 1, wherein the step of determining spatial alignment offsets comprises the steps of:
   (a) selecting a first one of said different channels as a reference channel;
   (b) selecting a different one of said different channels as a data channel, image signal data in the data channel to be aligned with image signal data in the reference channel;
   (c) producing a correlogram by processing image signal data from the reference channel with image signal data from the data channel;
   (d) determining a peak of the correlogram; and
   (e) comparing the peak of correlogram with image signal data in the reference channel to determine the spatial alignment offsets.

6. The method of claim 5, wherein the step of producing a correlogram comprises the step of processing image signal data from the reference channel with image signal data from the data channel in the frequency domain.

7. The method of claim 5, wherein the step of producing a correlogram comprises the step of processing image signal data from the reference channel with image signal data from the data channel in the spatial domain.

8. The method of claim 5, wherein the step of producing a correlogram comprises the step of processing a subset of image signal data from the reference channel with a subset of image signal data from the data channel, wherein the possible spatial alignment offsets correspond to the subsets.

9. The method of claim 5, wherein the step of preparing a correlogram comprises the step of using boundary data corresponding to image signal data the reference channel and image signal data in the data channel.

10. The method of claim 9, wherein the boundary data are generated using a two dimensional gradient operator.

11. The method of claim 1, wherein the step of aligning the image signal data comprises the step of convolving the image signal data using an interpolation kernel to enable image signal data to be aligned with sub-pixel resolution.

12. The method of claim 11, wherein the interpolation kernel is determined using a function approximation of the peak of a correlogram using a Taylor series expansion.

13. The method of claim 1, wherein the step of determining spectral crosstalk reduction coefficients comprises the step of imaging a control sample, wherein said control sample comprises a source substantially limited to a single one of the different channels.

14. The method of claim 13, wherein the control sample comprises at least one of a synthesized bead and a biological sample.

15. The method of claim 1, wherein the step of determining spectral crosstalk reduction coefficients comprises the step of employing a theoretical model of a crosstalk spectrum and a sensitivity of a camera used to capture an image of a sample to a stimulus of a spectrum, in producing the image signal data.

16. The method of claim 1, wherein the step of determining spectral crosstalk reduction coefficients comprises the step of solving linear equations.

17. The method of claim 16, wherein the step of solving linear equations comprises the step of utilizing a singular value decomposition.

18. The method of claim 1, wherein the step of applying the spectral crosstalk coefficients for spectral correction comprises the step of applying a linear equation.

19. A method for correcting errors in a multichannel signal, the multichannel signal comprising an ensemble of related signals used to produce images for different channels, wherein each signal is associated with a different channel and is intended to provide information from only one source, comprising the steps of:
   (a) aligning the signals in the ensemble relative to each other, such that when images produced from the signals are displayed, each image produced from a signal in the ensemble is substantially aligned with images produced from other signals in the ensemble;
   (b) determining spectral crosstalk corrections suitable for correcting channel-to-channel crosstalk between signals of the ensemble; and
   (c) applying the spectral crosstalk corrections to the signals associated with the different channels, to correct for the channel-to-channel crosstalk between the signals.

20. The method of claim 19, wherein the step of aligning comprises the step of applying:
   (a) horizontal and vertical spatial offsets derived from a calibration signal; and
   (b) constants that are accessed during the step of aligning, but which are not modified.

21. The method of claim 20, wherein the second class of constants comprises at least one of channel start columns for each signal, and inverted source coefficients.

22. The method of claim 20, wherein the step of applying the spectral crosstalk corrections comprises the step of employing constants that are accessed, but which are not modified.

23. The method of claim 19, wherein the step of aligning comprises the step of applying spatial corrections at a sub-pixel resolution.

24. The method of claim 19, further comprising the step of providing a calibration signal, wherein the step of aligning comprises the step of generating horizontal and vertical spatial offsets based upon a comparison of each signal in the ensemble with the calibration signal.

25. The method of claim 24, wherein the step of providing a calibration signal comprises the step of imaging a control sample having a single source.

26. The method of claim 24, wherein the step of providing a calibration signal further comprising the step of providing the calibration signal when the multichannel system is initialized.

27. The method of claim 24, wherein the step of providing a calibration signal further comprising the step of providing the calibration signal periodically during the use of the multichannel system.

28. The method of claim 24, wherein each signal in the ensemble comprises image data, and horizontal and vertical spatial offsets are determined for each pixel of the image data, to align the images in the different channels.

29. The method of claim 28, wherein the step of aligning, for successive signals in the ensemble that are processed, comprises the steps of:
   (a) detecting a boundary of a signal currently being processed;
   (b) preparing a correlogram based on the boundary and a reference signal, thereby enabling location of a peak in the correlogram;
   (c) repositioning the signal currently being processed, to correspond to the peak of the correlogram.

30. The method of claim 29, wherein the step of detecting a boundary of the signal currently being processed comprises the step of using a two-dimensional gradient operator to suppress flat surfaces and to enhance object boundaries.

31. The method of claim 29, wherein the step of preparing a correlogram based on the boundary and the reference signal comprises the step of preparing a correlogram in a frequency domain.

32. The method of claim 31, wherein the step of preparing a correlogram in the frequency domain comprises the steps of:
   (a) performing a Fourier Transform of boundary data for a selected signal from the ensemble and a Fourier Transform of the reference signal;
   (b) multiplying a result of the Fourier Transform of the boundary data for the selected signal by a result of the Fourier Transform of the reference signal to generate a product; and
   (c) performing an inverse Fourier Transform of the product.

33. The method of claim 29, wherein the step of preparing a correlogram based on the boundary and the reference signal comprises the step of preparing a correlogram in the spatial domain.

34. The method of claim 33, wherein the step of preparing a correlogram in the spatial domain comprises the steps of performing signal processing upon a subset of possible spatial alignment offsets.

35. The method of claim 29, wherein groups of image data in each channel of the multichannel system are processed together, such that a cumulative correlogram is generated for each successive channel that is processed.

36. The method of claim 29, wherein the step of aligning further comprises the step of reconstructing each signal in the ensemble by interpolating a position of the image produced with the signal to a fraction of a pixel.

37. The method of claim 36, wherein the step of reconstructing each signal comprises the step of applying a two-dimensional interpolation.

38. The method of claim 37, wherein the step of applying a two-dimensional interpolation comprises the step of computing a new amplitude value for each pixel based on a weighted sum of a group of surrounding pixels.

39. The method of claim 38, wherein the step of computing a new amplitude value for each pixel is based on a weighted sum of a group of nine pixels, eight pixels of which surround an origin pixel.

40. The method of claim 38, wherein the step of computing a new amplitude value for each pixel comprises the step of applying a matrix of coefficients to each pixel value, wherein a sum the of the coefficients in the matrix is equal to 1.0.

41. The method of claim 29, further comprising the step of determining the peak of the correlogram by employing a Taylor series expansion, eigenvalues, and eigenvectors.

42. The method of claim 24, further comprising the step of storing the signals for a period of time, wherein the step of applying spectral crosstalk corrections comprises the step of applying spectral crosstalk corrections to at least one of the signals that have been stored for the period of time.

43. The method of claim 19, wherein the step of aligning comprises the step of aligning the signal in real time.

44. The method of claim 19, further comprising the step of storing the signals for a period of time, wherein the step of aligning the signals in the ensemble comprises the step of aligning signals that have been stored for the period of time.

* * * * *